US010596094B2

(12) United States Patent
Pawelek

(10) Patent No.: US 10,596,094 B2
(45) Date of Patent: Mar. 24, 2020

(54) COMPOSITIONS AND METHODS FOR REDUCING SKIN PIGMENTATION

(71) Applicant: Yale University, New Haven, CT (US)

(72) Inventor: John Mason Pawelek, Hamden, CT (US)

(73) Assignee: YALE UNIVERSITY, New Haven, CT (US)

(*) Notice: Subject to any disclaimer, the term of this patent is extended or adjusted under 35 U.S.C. 154(b) by 0 days.

(21) Appl. No.: 14/772,151

(22) PCT Filed: Mar. 7, 2014

(86) PCT No.: PCT/US2014/021738
§ 371 (c)(1),
(2) Date: Sep. 2, 2015

(87) PCT Pub. No.: WO2014/138578
PCT Pub. Date: Sep. 12, 2014

(65) Prior Publication Data
US 2016/0015617 A1 Jan. 21, 2016

Related U.S. Application Data

(60) Provisional application No. 61/775,188, filed on Mar. 8, 2013.

(51) Int. Cl.
A61K 8/60 (2006.01)
A61Q 19/02 (2006.01)
C12N 15/113 (2010.01)
A61K 8/64 (2006.01)

(52) U.S. Cl.
CPC .............. A61K 8/602 (2013.01); A61K 8/606 (2013.01); A61K 8/64 (2013.01); A61Q 19/02 (2013.01); C12N 15/1137 (2013.01); C12Y 204/99001 (2013.01); C12Y 204/99006 (2013.01); A61K 2800/782 (2013.01); C12N 2310/14 (2013.01); C12N 2320/00 (2013.01)

(58) Field of Classification Search
None
See application file for complete search history.

(56) References Cited

U.S. PATENT DOCUMENTS

| 2005/0222076 | A1* | 10/2005 | Kawamura | A61K 8/606 514/47 |
| 2007/0160554 | A1* | 7/2007 | Kempers | A61K 8/606 424/70.13 |
| 2007/0166251 | A1* | 7/2007 | Dayan | A61K 8/34 424/62 |
| 2008/0254130 | A1* | 10/2008 | Gupta | A61K 8/35 424/489 |
| 2010/0143289 | A1* | 6/2010 | Cohen | A61K 8/365 424/85.1 |
| 2011/0250157 | A1* | 10/2011 | Perricone | A61K 8/365 424/62 |

FOREIGN PATENT DOCUMENTS

| EP | 1378224 A1 | 1/2004 |
| FR | 2891737 A1 | 4/2007 |
| GB | 1422642 | 12/1972 |
| JP | 01-163112 A | 6/1989 |
| JP | 01163112 A | 6/1989 |
| WO | 00/06115 A1 | 2/2000 |
| WO | 2008/082525 A1 | 7/2008 |
| WO | WO 2009/113861 | 9/2009 |
| WO | 2011/138687 A2 | 10/2011 |
| WO | WO 2012/103038 | 8/2012 |
| WO | WO 2012/156927 | 11/2012 |

OTHER PUBLICATIONS

Miyazaki et al., CMP substitutions preferentially inhibit polysialic acid synthesis. Glycobiology, 2008, 18:187-194.
Shibuya et al., The Elderberry (*Sambucus nigra* L.) Bark Lectin Recognizes the Neu5Ac(a2-6)Gal/GalNAc Sequence*. The Journal of Biological Chemistry, 1987, 262:1596-1601.
Scott et al., Prostaglandin E2 regulates melanocyte dendrite formation through activation of PKCζ. 2007, Exp Cell Res 313:3840-50.
Scott et al., Semaphorin 7a Promotes Spreading and Dendricity in Human Melanocytes through β1-Integrins. 2008, J Invest Dermatol 128:151-61.
Scott et al., Demonstration of Melanosome Transfer by a Shedding Microvesicle Mechanism. 2012, J Invest Dermatol 132(4):1073-4.
Singh et al., Bone morphogenetic proteins differentially regulate pigmentation in human skin cells. 2012, J Cell Sci 125(Pt 18):4306-19.
Lin et al., Stachybotrydial, a potent inhibitor of fucosyltransferase and sialyltransferase. 2005, Biochem Biophys Res Commun, 331:953-957.
Izumi et al., Synthesis of Bisubstrate and Donor Analogues of Sialyltransferase and Their Inhibitory Activities. 2005, J Org Chem, 70:8817-8824.
Chang et al., Lithocholic acid analogues, new and potent a-2,3-sialyltransferase inhibitors{. 2006, Chem Commun, 14:629-931.
Chang et al., Soyasaponin I decreases the expression of a2,3-linked sialic acid on the cell surface and suppresses the metastatic potential of B16F10 melanoma cells. 2006, Biochem Biophys Res Commun, 341:614-619.
Hsu et al., Soyasaponin-I-modified invasive behavior of cancer by changing cell surface sialic acids. 2005, Gynecol Oncol, 96:415-422.
Kleineidam et al., Studies on the inhibition of sialyl- and Galactosyltransferase. 1997, Glycoconj J, 14:57-66.

(Continued)

Primary Examiner — Kevin S Orwig
(74) Attorney, Agent, or Firm — Riverside Law LLP

(57) ABSTRACT

The present invention provides compositions and methods for reducing skin pigmentation. The invention comprises inhibitors of sialyltransferase, inhibitors of oligosaccharide formation or oligosaccharide activity, and methods of using such inhibitors. In certain embodiments, the invention comprises inhibiting the formation and/or activity of Neu5Ac (α2,6)Gal/GalNAc-containing oligosaccharides.

4 Claims, 11 Drawing Sheets

(56) References Cited

OTHER PUBLICATIONS

Xia et al., Synthesis of Fluorinated Mucin Core 2 Branched Oligosaccharides with the Potential of Novel Substrates and Enzyme Inhibitors for Glycosyltransferases and Sulfotransferases. 2006, J Org Chem, 71:3696-3706.
Lee et al., The Hexapeptide Inhibitor of GaⅠ 1,3GalNAc-specific 2,3-Sialyltransferase as a Generic Inhibitor of Sialyltransferases*. 2002, J Biol Chem, 277:49341-49351.
Gouyer et al., Inhibition of the glycosylation and alteration in the intracellular trafficking of mucins and other glycoproteins by GalNAcalpha-O-bn in mucosal cell lines: an effect mediated through the intracellular synthesis of complex GalNAcalpha-O-bn oligosaccharides. Front Biosci. Oct. 1, 2001; 6:D1235-44.
Azuma et al., Decrease in cell surface sialic acid in etoposidetreated Jurkat cells and the role of cell surface Sialidase. 2000, Glycoconj J, 17:301-306.
Delannoy et al., Benzyl-N-acetyl-a-o-galactosaminide inhibits the sialylation and the secretion of mucins by a mucin secreting HT-29 cell subpopulation. 1996, 13:717-726.
Kajihara et al., Characterization of inhibitory activities and binding mode of synthetic 6'-modified methyl N-acetyl-B-lactosaminide toward rat liver CMP-D-NeuSAc: D-galactoside-(2--6)-a-D-sialyltransferase. 1993, Carbohydr Res, 247:179-193.
Cambron et al., Inhibition of CMP-N-Acetylneuraminic Acid: Lactosylceramide Sialyltransferase by Nucleotides, Nucleotide Sugars and Nucleotide Dialdehydes. 1993, Biochem Biophys Res Commun, 193:585-590.
Kilton et al., Brief Communication: Nucleotide-Induced Inhibition of Surface Sialyl Transferase Activity on Cultured Burkitt's Lymphoma Cells 1,2,3. 1977, J Natl Cancer Inst., 58:1479-1481.
Kijima-Suda et al., Possible Mechanism of Inhibition of Experimental Pulmonary Metastasis of Mouse Colon Adenocarcinoma 26 Sublines by a Sialic AcidrNucleoside Conjugate. 1988, Cancer Res, 48:3728-3732.
Hindenburg et al., Effects of Pyrimidine Antagonists on Sialic Acid Regeneration in HL-60 Cells1. 1985, Cancer Res, 45:3048-3052.
Guette et al., Inhibition of glycosyltransferases by bis-(p-nitrophenyl)phosphate general effect and relation to their membrane integration. 1983, Biochimie, pp. 563-567.
Wang et al., The Cotranslational Maturation of the Type I Membrane Glycoprotein Tyrosinase: The Heat Shock Protein 70 System Hands Off to the Lectin-based Chaperone System. 2003, Bioorg Med Chem, 11:4217-4224.
Kaku et al, Elderberry Bark Lectins Evolved to Recognize Neu5Aca2,6Gal/GalNAc Sequence from a Gal/GalNAc Binding Lectin Through the Substitution of Amino-Acid Residues Critical for the Binding to Sialic Acid. 2007, J Biochem, 142:3.
Ujvari et al., Translation rate of human tyrosinase determines its N-linked glycosylation level. J Biol Chem. Feb. 23, 2001; 276(8):5924-31.
Imokawa et al., Analysis of carbohydrate properties essential for melanogenesis in tyrosinases of cultured malignant melanoma cells by differential carbohydrate processing inhibition. J Invest Dermatol. 1990; 95:39-49. Reviews Glucosamine Inhibition of Core Oligosaccharide Synthesis and Pigmentation.
Mishima et al., Selective aberration and pigment loss in melanosomes of malignant melanoma cells in vitro by glycosylation inhibitors: premelanosomes as glycoprotein. J Invest Dermatol 1983 81:106-114.
Imokawa et al., Functional analysis of tyrosinase isozymes of cultured malignant melanoma cells during the recovery period following interrupted melanogenesis induced by glycosylation inhibitors. J Invest Dermatol 1984; 83:196-201.
Imokawa et al., Analysis of tyrosinases as asparagin-linked oligosaccharides by concanavalin A lectin chromatography: appearance of new segment of tyrosinases in melanoma cells following interrupted melanogenesis induced by glycosylation inhibitors. J Invest Dermatol 1985; 85:165-168.

Ohkura et al., Purification of hamster melanoma tyrosinases and structural studies of their asparagine-linked sugar chains. Arch Biochem Biophys1984; 235:63-77.
Imokawa et al., Loss of melanogenic properties in tyrosinases induced by glucosylation inhibitors within malignant melanoma cells. Cancer Res 1982; 42: 1994-2002.
Imokawa et al., Importance of glycoproteins in the initiation of melanogenesis: an electron microscopic study of B-16 melanoma cells after release from inhibition of glycosylation. J Invest Dermatol 1986; 87:319-325.
Mishima et al., Control of melanogenesis and melanoma oncogenesis. Prog Clin Biol Res. 1988; 256:127-141.
Takahashi et al., Rapid and reversible inhibition of tyrosinase activity by glucosidase inhibitors in human melanoma cells. J Invest Dermatol 1992; 98:481-487.
Petrescu et al., Inhibition of N-Glycan Processing in B16 Melanoma Cells Results in Inactivation of Tyrosinase but Does Not Prevent Its Transport to the Melanosome. J Biol Chem 1997; 272:15796-15803.
Negreoiu et al., Investigation of the intracellular transport of tyrosinase and tyrosinase related protein (TRP)-1. The effect of endoplasmic reticulum (ER)-glucosidases inhibition. Cell Mol Biol (Noisy-le-grand). 1999; 45:1001-1010.
Negroiu et al., Protein specific N-glycosylation of tyrosinase and tyrosinase-related protein-1 in B16 mouse melanoma cells. Biochem J 1999; 344:659-665.
Branza-Nichita et al. Mutations at critical N-glycosylation sites reduce tyrosinase activity by altering folding and quality control. J Biol Chem 2000; 275:8169-8175.
Branza-Nichita et al., N-glycosylation processing and glycoprotein folding-lessons from the tyrosinase-related proteins. Chem Rev 2003; 100:4697-4712.
Mosse et al., Tyrosinase degradation via two pathways during reverse translocation to the cytosol. Biochem Biophys Res Commun 2001; 285:313-319.
Olivares et al., Conformation-dependent post-translational glycosylation of tyrosinase. Requirement of a specific interaction involving the CuB metal binding site. J Biol Chem 2003; 278:15735-15743.
Svedine et al., Carbohydrates act as sorting determinants in ER-associated degradation of tyrosinase. J Cell Sci 2004; 117:2937-2949.
Lavado et al. Molecular basis of the extreme dilution mottled mouse mutation: a combination of coding and noncoding genomic alterations. J Biol Chem 2005; 280: 4817-4824.
Maresca et al., Ferritin light chain down-modulation generates depigmentation in human metastatic melanoma cells by influencing tyrosinase maturation. J Cell Physiol 2006; 206:843-848.
Jimbow et al. Yamashita, T. Assembly, target-signaling and intracellular transport of tyrosinase gene family proteins in the initial stage of melanosome biogenesis. Pigment Cell Res 2000; 13:222-229.
Xu et al. Diverse roles of conserved asparagine-linked glycan sites on tyrosinase family glycoproteins. Exp Cell Res 2001; 267:115-125.
Aroca et al., The action of glycosylases on dopachrome (2-carboxy-2,3-dihydroindole-5,6-quinone) tautomerase. Biochem J 1992; 284:109-113.
Hornyak et al., Cell-density-dependent regulation of expression and glycosylation of dopachrome tautomerase/tyrosinase-related protein-2. J Invest Dermatol 2000; 115: 106-112.
Negroiu et al., The inhibition of early N-glycan processing targets TRP-2 to degradation in B16 melanoma cells. J Biol Chem 2003; 278:27035-27042.
Yasumoto et al., Epitope mapping of the melanosomal matrix protein gp100 (PMEL17): rapid processing in the endoplasmic reticulum and glycosylation in the early Golgi compartment. J Biol Chem 2004; 279:28330-28338.
Lazova et al., Autophagy in cutaneous malignant melanoma. J. Cutan Pathol, 2010; 37:256-268.
Valencia et al., Sialylated core 1 O-glycans influence the sorting of Pmel17/gp100 and determine its capacity to form fibrils. J Biol Chem. 2007, 282:11266-80.
Schauer et al., Sialic acids as regulators of molecular and cellular interactions. Curr Opin Struct Biol. 2009, 19:507-514.

(56) References Cited

OTHER PUBLICATIONS

Choi et al., Influence of N-glycan processing disruption on tyrosinase and melanin synthesis in HM3KO melanoma cells. Exp Dermatol. 2007; 16:110-7.
Pawelek et al., Altered N-glycosylation in macrophage x melanoma fusion hybrid. Cell Mol Biol (Noisy-le-grand). 1999; 45:1011-27.
Harduin-Lepers et at., The human sialyltransferase family. Biochimie. 2001; 83:727-37.
Mintel-Database Accession No. 78323 GNPD [Online]; Nov. 2000, Collistar: "Anti-Ageing Cream Range".
Database Accession No. 114-49368 STN Chemical Abstrac [Online]; 1989, Horiuchi et al.: "Skin cosmetics containing N-acetylneuraminic acid-bound oligosaccharides".
Office Action cited in corresponding Japanese Patent Application No. 2015-561711, dated Oct. 17, 2017.

* cited by examiner

COMPOSITIONS AND METHODS FOR REDUCING SKIN PIGMENTATION

CROSS-REFERENCE TO RELATED APPLICATIONS

This application is the U.S. national stage application filed under 35 U.S.C. § 371 claiming benefit to International Patent Application No. PCT/US14/021738, filed Mar. 7, 2014, which is entitled to priority under 35 U.S.C. § 119(e) to U.S. Provisional Application No. 61/775,188, filed Mar. 8, 2013, each of which is hereby incorporated by reference in its entirety.

BACKGROUND OF THE INVENTION

As humans we are social beings where uneven or asymmetric pigmentation on the face and other areas of the body can cause lowered self-esteem, depression, problems with social status and reduced productivity in the workplace (Balkrishnan et al., 2006, Int J Dermatol 45:111-5). Hyperpigmentation of the skin is a common condition for which many individuals seek corrective treatment. It is the result of increased cutaneous melanin, sometimes asymmetrically in a spot or covering particular regions of skin; in other cases with bilateral symmetry. This can be caused by increased melanin synthesis and transfer to keratinocytes; a greater number of melanocytes; and in some cases by melanophages, melanin-containing macrophages that accumulate melanin through phagocytosis. Hyperpigmented regions are brown to blue-grey. There are many causes of hyperpigmentation, some of the most common being melasma, post-inflammatory hyperpigmentation (PIH) and solar lentigenes (liver spots).

Melanocytes are the pigment producing cells of the skin. Melanins, the chief pigments, are synthesized by a group of enzymes located in small cellular bodies known as melanosomes in the cytoplasm of melanocytes. Melanocytes are located in the basal layer of the epidermis in close contact with keratinocytes to which they donate melanin. On the average, humans have about the same number of melanocytes per $mm^2$ of skin regardless of ethnic background. Each melanocyte is associated with about 36 keratinocytes in an "epidermal-melanin unit". Normally it is not the number of melanocytes but the activity of the melanocytes, including synthesis of melanin and its transfer to keratinocytes that determines our actual skin color and intensity. Melanosomes laden with melanin are transferred from melanocytes to surrounding keratinocytes, the most abundant cells of the skin, imparting coloration and sun protection to the skin (FIG. 1).

Melanosome transfer to keratinocytes is a unique biological process involving organelle donation from one cell to another and is a crucial step in skin pigmentation. Individuals with defects in this process can have markedly reduced skin melanin content. The process involves the attachment of melanocytes to keratinocytes; transfer of melanosomes into keratinocytes; and, in skin, trafficking to the supranuclear area of the keratinocyte. There is growing information on melanocyte-keratinocyte transfer regarding cell biology, cytokine and hormonal signaling pathways and the role of peptides and proteins (Scott et al., 2007, Exp Cell Res 313:3840-50; Scott et al., 2008, J Invest Dermatol 128:151-61; Scott, 2012, J Invest Dermatol 132(4):1073-4; Singh et al., 2012, J Cell Sci 125(Pt 18):4306-19). However, there remains a need in the art for compositions and methods for treating and preventing hyperpigmentation. The present invention satisfies this unmet need.

SUMMARY OF THE INVENTION

The present invention provides a composition for reducing skin pigmentation. The composition comprises an inhibitor of sialyltransferase activity, an inhibitor of oligosaccharide formation, or an inhibitor of oligosaccharide activity. In one embodiment, the inhibitor of sialyltransferase activity comprises an inhibitor of β-galactoside α2,6'-Sialyltransferase I (ST6Gal.I) activity. In one embodiment, the inhibitor reduces the expression of ST6Gal.I in a cell. In one embodiment, the inhibitor reduces the formation of Neu5Ac(α2,6)Gal/GalNAc-containing oligosaccharides. In one embodiment, the inhibitor is an inhibitor of Neu5Ac(α2,6)Gal/GalNAc-containing oligosaccharide activity.

In one embodiment, the inhibitor is at least one of a nucleic acid, a siRNA, an antisense nucleic acid, a ribozyme, a peptide, a small molecule, an antagonist, an aptamer, and a peptidomimetic. In one embodiment, the inhibitor is selected from the inhibitors listed in Table 1. In one embodiment, the inhibitor is selected from the inhibitors listed in Table 2.

In one embodiment, the inhibitor is at least one of cytidine, cytidine monophosphate N-acetylneuraminic acid, 6'-sialylgalactose, 6'-sialyl N-acetylgalactosamine, 6'-sialyllactose, 3'-sialyllactose, or N-acyl-neuraminyl. In one embodiment, the inhibitor is cytidine or an analogue thereof.

In one embodiment, the inhibitor is 6'-sialyllactose. In one embodiment, the inhibitor is 3'-sialyllactose.

In one embodiment, the composition comprises at least two inhibitors. In one embodiment, the composition comprises 6'-sialyllactose and cytidine, or an analogue thereof. In one embodiment, the composition comprises 3'-sialyllactose and cytidine, or an analogue thereof. In one embodiment, the composition comprises 6'-sialyllactose and 3'-sialyllactose. In one embodiment, the composition comprises 6'-sialyllactose, 3'-sialyllactose and cytidine, or an analogue thereof. In one embodiment, the effects of the two or more inhibitors are synergistic.

The present invention provides a composition for reducing skin pigmentation comprising cytidine, or an analog thereof. In one embodiment, the composition further comprises is 6'-sialyllactose. In one embodiment, the composition further comprises 3'-sialyllactose.

The present invention provides a method for reducing skin pigmentation comprising administering to a subject an effective amount of an inhibitor selected from a group consisting of an inhibitor of sialyltransferase activity, an inhibitor of oligosaccharide formation and an inhibitor of oligosaccharide activity.

In one embodiment, the inhibitor of sialyltransferase activity comprises an inhibitor of β-galactoside α2,6'-Sialyltransferase I (ST6Gal.I) activity. In one embodiment, the inhibitor reduces the expression of ST6Gal.I in a cell. In one embodiment, the inhibitor reduces the formation of Neu5Ac(α2,6)Gal/GalNAc-containing oligosaccharides. In one embodiment, the inhibitor is an inhibitor of Neu5Ac(α2,6)Gal/GalNAc-containing oligosaccharide activity.

In one embodiment, the inhibitor is at least one of a nucleic acid, a siRNA, an antisense nucleic acid, a ribozyme, a peptide, a small molecule, an antagonist, an aptamer, and a peptidomimetic. In one embodiment, the inhibitor is selected from the inhibitors listed in Table 1. In one embodiment, the inhibitor is selected from the inhibitors listed in Table 2.

In one embodiment, the inhibitor is at least one of cytidine, cytidine monophosphate N-acetylneuraminic acid, 6'-sialylgalactose, 6'-sialyl N-acetylgalactosamine, 6'-sialyllactose, 3'-sialyllactose, or N-acyl-neuraminyl. In one embodiment, the inhibitor is cytidine or an analogue thereof.

In one embodiment, the inhibitor is 6'-sialyllactose. In one embodiment, the inhibitor is 3'-sialyllactose.

In one embodiment, the method comprises administering a composition comprising at least two inhibitors. In one embodiment, the composition comprises 6'-sialyllactose and cytidine, or an analogue thereof. In one embodiment, the composition comprises 3'-sialyllactose and cytidine, or an analogue thereof. In one embodiment, the composition comprises 6'-sialyllactose and 3'-sialyllactose. In one embodiment, the composition comprises 6'-sialyllactose, 3'-sialyllactose and cytidine, or an analogue thereof. In one embodiment, the effects of the two or more inhibitors are synergistic.

In one embodiment, the method comprises administering a first composition comprising a first inhibitor selected from a group consisting of an inhibitor of sialyltransferase activity, an inhibitor of oligosaccharide formation and an inhibitor of oligosaccharide activity; and administering a second composition comprising an inhibitor selected from a group consisting of an inhibitor of sialyltransferase activity, an inhibitor of oligosaccharide formation and an inhibitor of oligosaccharide activity. In one embodiment, the first composition comprises a first inhibitor selected from the group consisting of cytidine, cytidine monophosphate N-acetylneuraminic acid, 6'-sialylgalactose, 6'-sialyl N-acetylgalactosamine, 6'-sialyllactose, 3'-sialyllactose, and N-acyl-neuraminyl. In one embodiment, the second composition comprises a second inhibitor selected from the group consisting of cytidine, cytidine monophosphate N-acetylneuraminic acid, 6'-sialylgalactose, 6'-sialyl N-acetylgalactosamine, 6'-sialyllactose, 3'-sialyllactose, and N-acyl-neuraminyl.

In one embodiment, the method comprises administering the composition to the skin of the subject. In one embodiment, the subject has hyperpigmentation of at least a region of skin. In one embodiment, the method inhibits melanin production. In one embodiment, the method inhibits the transfer of a melanosome from a melanocyte of the subject to a keratinocyte of the subject. In one embodiment, the subject is human.

The present invention provides a method for reducing skin pigmentation comprising administering to a subject an effective amount of cytidine, or an analog thereof. In one embodiment, the method further comprises administering to the subject an effective amount of 6'-sialyllactose. In one embodiment, the method further comprises administering to the subject an effective amount of 3'-sialyllactose.

The present invention provides a kit for reducing skin pigmentation. The kit comprises instructional material and a composition for reducing skin pigmentation comprising an inhibitor selected from a group consisting of an inhibitor of sialyltransferase activity, an inhibitor of oligosaccharide formation and an inhibitor of oligosaccharide activity.

In one embodiment, the inhibitor of sialyltransferase activity comprises an inhibitor of β-galactoside α2,6'-Sialyltransferase I (ST6Gal.I) activity. In one embodiment, the inhibitor reduces the expression of ST6Gal.I in a cell. In one embodiment, the inhibitor reduces the formation of Neu5Ac (α2,6)Gal/GalNAc-containing oligosaccharides. In one embodiment, the inhibitor is an inhibitor of Neu5Ac(α2,6) Gal/GalNAc-containing oligosaccharide activity.

In one embodiment, the inhibitor is at least one of a nucleic acid, a siRNA, an antisense nucleic acid, a ribozyme, a peptide, a small molecule, an antagonist, an aptamer, and a peptidomimetic. In one embodiment, the inhibitor is selected from the inhibitors listed in Table 1. In one embodiment, the inhibitor is selected from the inhibitors listed in Table 2.

In one embodiment, the inhibitor is at least one of cytidine, cytidine monophosphate N-acetylneuraminic acid, 6'-sialylgalactose, 6'-sialyl N-acetylgalactosamine, 6'-sialyllactose, 3'-sialyllactose, or N-acyl-neuraminyl. In one embodiment, the inhibitor is cytidine or an analogue thereof.

In one embodiment, the inhibitor is 6'-sialyllactose. In one embodiment, the inhibitor is 3'-sialyllactose.

In one embodiment, the composition comprises at least two inhibitors. In one embodiment, the composition comprises 6'-sialyllactose and cytidine, or an analogue thereof. In one embodiment, the composition comprises 3'-sialyllactose and cytidine, or an analogue thereof. In one embodiment, the composition comprises 6'-sialyllactose and 3'-sialyllactose. In one embodiment, the composition comprises 6'-sialyllactose, 3'-sialyllactose and cytidine, or an analogue thereof. In one embodiment, the effects of the two or more inhibitors are synergistic.

In one embodiment the kit comprises a first composition comprising a first inhibitor selected from a group consisting of an inhibitor of sialyltransferase activity, an inhibitor of oligosaccharide formation and an inhibitor of oligosaccharide activity; and a second composition comprising an inhibitor selected from a group consisting of an inhibitor of sialyltransferase activity, an inhibitor of oligosaccharide formation and an inhibitor of oligosaccharide activity. In one embodiment, the first composition comprises a first inhibitor selected from the group consisting of cytidine, cytidine monophosphate N-acetylneuraminic acid, 6'-sialylgalactose, 6'-sialyl N-acetylgalactosamine, 6'-sialyllactose, 3'-sialyllactose, and N-acyl-neuraminyl. In one embodiment, the second composition comprises a second inhibitor selected from the group consisting of cytidine, cytidine monophosphate N-acetylneuraminic acid, 6'-sialylgalactose, 6'-sialyl N-acetylgalactosamine, 6'-sialyllactose, 3'-sialyllactose, and N-acyl-neuraminyl.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A and FIG. 3B, is a set of images depicting the results of experiments illustrating the histochemical staining of melanocytes from sequential sections of the same skin biopsy. Sections were stained through standard immunoperoxidase methods using a brown chromagen. Counter-staining was with hematoxylin. FIG. 3A depicts a section stained with EBL/SNA lectin showing staining of melanocytes. FIG. 3B depicts a sequential section stained with MAAII lectin. Melanocyte nuclei are marked with white asterisks.

FIG. 4A and FIG. 4B, is a set of images depicting the results of experiments illustrating a melanocyte in contact with a keratinocyte in co-culture. Cultures were stained with EBL/SNA by standard histochemical techniques using a red chromagen and photographed through a Zeiss light microscope. FIG. 4A is a low power photo showing EBL/SNA staining of melanocyte plasma membrane. FIG. 4B is a high power photo of the filapodial contact points (asterisk).

FIG. 5A and FIG. 5B, is a set of images depicting the results of experiments demonstrating the effects of L-cytidine (25 micromolar) on EBL staining and melanin content of human melanocyte-keratinocye co-cultures. Cultures were incubated 72 h with L-cytidine (25 micromolar), rinsed in BSS, fixed with paraformaldehyde, rinsed again with BSS and stained with EBL (red chromagen) using standard IHC procedures. Counterstaining was with hematoxylin. Random fields were photographed with a Zeiss Axioskop 40 light microscope equipped with a Spot Flex digital camera. Using Photoshop tools, dendrites were cut and pasted into the treatment groups herein. The composite images were then enhanced together with automatic contrast and brightening tools. FIG. 5A depicts untreated controls; FIG. 5B depicts EBL stained, L-cytidine treated.

FIG. 7A through FIG. 7D, depicts the results of experiments demonstrating the effects of cytidine, 6'-SL and 3'-SL on melanin content of melanocyte-keratinocyte co-cultures. Cells were incubated for 72 h with inhibitors, fixed with paraformaldehyde and stained for melanin with the Fontana-Masson silver stain to visualize melanin (Kwon-Chung et al., 1981, J Clin Microbiol, 13:383-387). Random fields were photographed and arranged into treatment groups with Photoshop tools. All images were enhanced together with automatic contrast and brightening tools. FIG. 7A depicts an untreated control (50 micromolar); FIG. 7B depicts cytidine treated cells (50 micromolar); FIG. 7C depicts 6'-SL treated cells (50 micromolar); FIG. 7D depicts 3'-SL treated cells (50 micromolar).

FIG. 8A and FIG. 8B, are a set of graphs depicting the results of experiments measuring the melanin content (FIG. 8A) and tyrosinase activity (FIG. 8B) in melanocyte-keratinocyte co-cultures. The dashed line indicates the $t_0$ levels at initiation of the experiment. Cases where melanin content was significantly greater than that expected for Bliss Additivity are indicated by (*) ($p=\leq0.06$); (**) ($p=\leq0.01$).

FIG. 9A and FIG. 9B, are a set of images depicting the results of experiments demonstrating the effects of cytidine in combination with 3'-SL on melanocyte-keratinocyte interactions and melanosome transfer. Cells were incubated 72 h with cytidine+3'-SL, fixed in paraformaldehyde, stained for melanin with the Fontana-Masson silver stain (Kwon-Chung et al., 1981, J Clin Microbiol, 13:383-387). Images were photographed and arranged into treatment groups with Photoshop tools. The images were enhanced together in the same layer with Photoshop automatic contrast and brightening tools. FIG. 9A depicts an untreated control. FIG. 9B depicts cells treated with cytidine (15 micromolar)+3'-SL (15 micromolar).

FIG. 11A and FIG. 11B, is a set of graphs depicting the results of experiments illustrating the effects of siRNAs for ST6 and ST3 on melanin production (FIG. 11A) and tyrosinase activity (FIG. 11B) in cultured human melanocytes, demonstrating that ST6 siRNA and, to a lesser extent ST3 siRNA, reduced melanin production (UT=untreated control).

DETAILED DESCRIPTION

Figure 1:
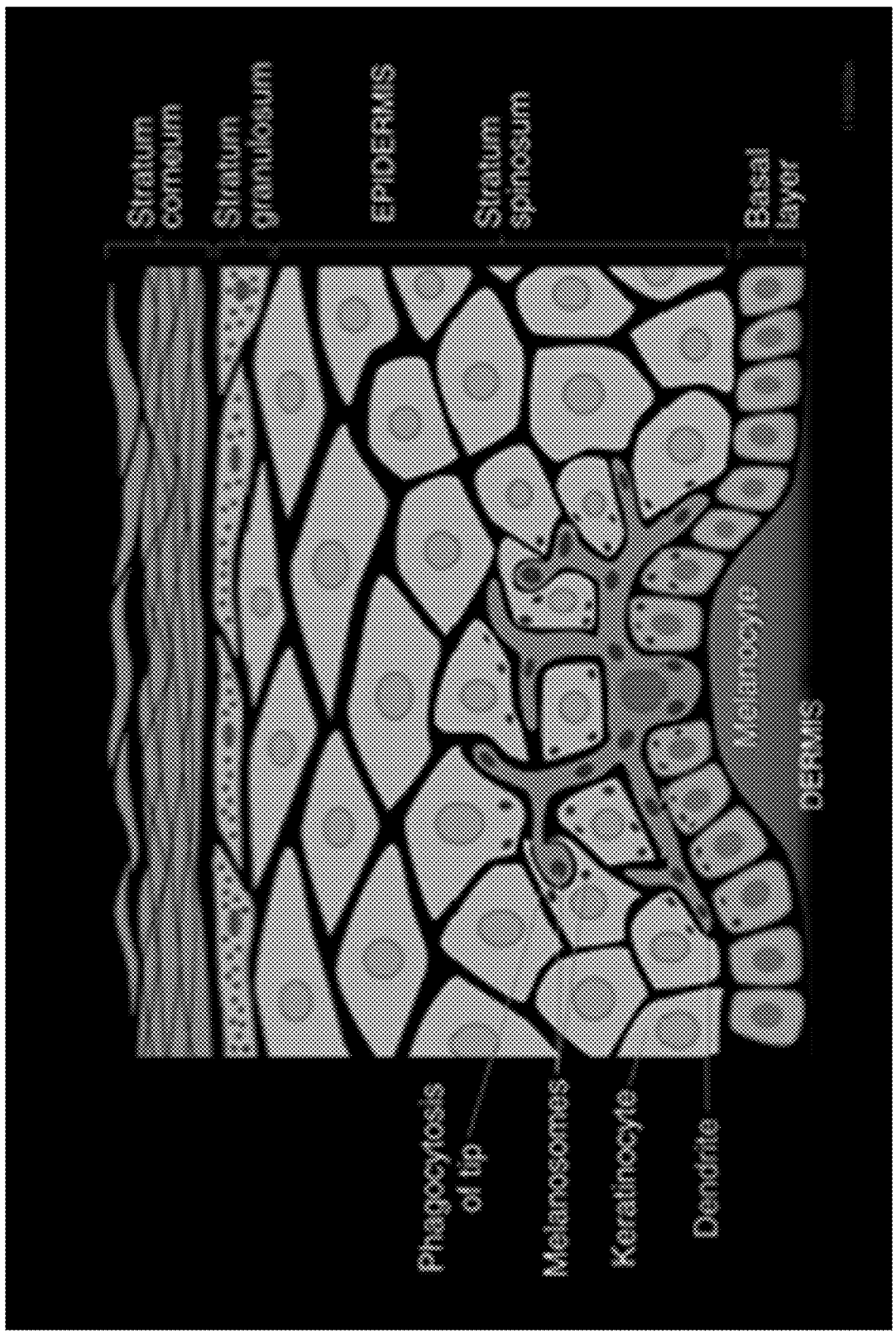
FIG. 1 is a schematic diagram of the pigmentary system in human skin. Shown is the domain of a single melanocyte and surrounding keratinocytes to which it transfers its melanosomes. Melanosomes are transferred through the melanocyte dendrites. This is referred to as an epidermal-melanin unit.

The present invention relates generally to compositions and methods for reducing skin pigmentation. The invention is used, for example, for treating and/or preventing excess pigmentation or uneven pigmentation. In certain embodiments, the invention treats and/or prevents hyperpigmentation.

In one embodiment, the present invention provides a composition for reducing skin pigmentation in a subject. In one embodiment, the composition comprises an inhibitor of sialyltransferase activity, an inhibitor of the activity of Neu5Ac(α2,6)Gal/GalNAc containing oligosaccharides, or a combination thereof.

In one embodiment, the present invention provides a method for reducing skin pigmentation. In one embodiment, the method comprises administering to a subject an effective amount of a composition comprises an inhibitor of sialyltransferase activity, an inhibitor of the activity of Neu5Ac (α2,6)Gal/GalNAc containing oligosaccharides, or a combination thereof. In certain embodiments, the method comprises administering the composition to a melanocyte of a subject.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease, or disorder, the frequency with which such a symptom is experienced by a patient, or both, are reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refers to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant cell" is a host cell that comprises a recombinant polynucleotide.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "sialyltransferase inhibitor," as used herein, refers to a composition or compound that inhibits sialyltransferase activity, either directly or indirectly, using any method known to the skilled artisan. A sialyltransferase inhibitor may be any type of compound, including but not limited to, a nucleic acid, peptide, small molecule, antagonist, aptamer, or peptidomimetic. A sialyltransferase inhibitor may inhibit one or more members of the sialyltransferase family, including, but not limited to, members of the β-galactoside α2,3-sialyltransferase (ST3Gal) family, β-galactoside α2,6-sialyltransferase (ST6Gal) family, GalNAc α2,6-sialyltransferase (ST6GalNAc) family, and the α2,8-sialyltransferase (ST8Sia) family.

The phrase "Neu5Ac(α2,6)Gal/GalNAc inhibitor," as used herein, refers to a composition or compound that inhibits Neu5Ac(α2,6)Gal/GalNAc activity, either directly or indirectly, using any method known to the skilled artisan. A Neu5Ac(α2,6)Gal/GalNAc inhibitor may be any type of compound, including but not limited to, a nucleic acid, peptide, small molecule, antagonist, aptamer, or peptidomimetic. As used herein, a "Neu5Ac(α2,6)Gal/GalNAc inhibitor" or "inhibitor of Neu5Ac(α2,6)Gal/GalNAc" also encompasses an inhibitor of conjugates comprising Neu5Ac(α2,6)Gal/GalNAc, including Neu5Ac(α2,6)Gal/GalNAc-containing oligosaccharides, Neu5Ac(α2,6)Gal/GalNAc-containing glycoconjugates, Neu5Ac(α2,6)Gal/GalNAc-containing glycolipids, Neu5Ac(α2,6)Gal/GalNAc-containing glycoproteins, and the like.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates generally to compositions and methods for reducing skin pigmentation. The invention is used, for example, for treating and/or preventing excess pigmentation or uneven pigmentation. In certain embodiments, the invention treats and/or prevents hyperpigmentation. Hyperpigmentation can arise from numerous causes, including, but not limited to, melasma, post-inflammatory hyperpigmentation (PIH), and solar lentigenes (liver spots).

The present invention is partly based upon the discovery of the role of Neu5Ac($\alpha$2,6)Gal/GalNAc, and in particular, Neu5Ac($\alpha$2,6)Gal/GalNAc containing oligosaccharides, in melanin formation and melanosome transfer. Neu5Ac($\alpha$2,6)Gal/GalNAc is a siaylated oligosaccharide sequence that is the terminal sequence for some membrane bound glycoconjugates. As presented herein, Neu5Ac($\alpha$2,6)Gal/GalNAc is found at the dendrites of a melanocyte and functions in transferring a melanosome from a melanocyte to a keratinocyte. Thus, the present invention comprises inhibiting the activity of Neu5Ac($\alpha$2,6)Gal/GalNAc and Neu5Ac($\alpha$2,6)Gal/GalNAc containing oligosaccharides, and/or the formation of Neu5Ac($\alpha$2,6)Gal/GalNAc and Neu5Ac($\alpha$2,6)Gal/GalNAc containing oligosaccharides for reducing skin pigmentation. The formation of Neu5Ac($\alpha$2,6)Gal/GalNAc and Neu5Ac($\alpha$2,6)Gal/GalNAc containing oligosaccharides is mediated by the activity of $\beta$-galactoside $\alpha$2,6'-Sialyltransferase I (ST6Gal.I), and thus the invention encompasses inhibiting the activity of ST6Gal.I for reducing skin pigmentation.

Further, it is described herein that inhibition of the expression of sialyltransferases, including, for example ST3Gal and ST6Gal, reduces skin pigmentation. Thus, the present invention encompasses inhibiting the expression, activity, or both of sialyltransferases for reducing skin pigmentation.

In one embodiment, the present invention provides a composition for reducing skin pigmentation in a subject, wherein the composition comprises an inhibitor of oligosaccharide formation. In one embodiment, the present invention provides a composition for reducing skin pigmentation in a subject, wherein the composition comprises an inhibitor of oligosaccharide activity. In one embodiment, the composition inhibits the formation and/or function of glycosylated oligosaccharides. As described herein, certain oligosaccharides, observed at melanocyte dendrites are found to be involved in melanin production and melanosome transfer.

In one embodiment, the present invention provides a composition for reducing skin pigmentation in a subject. In one embodiment, the composition comprises an inhibitor of sialyltransferase activity, an inhibitor of the activity of Neu5Ac($\alpha$2,6)Gal/GalNAc containing oligosaccharides, or a combination thereof.

As described herein, Neu5Ac($\alpha$2,6)Gal/GalNAc is a terminal siaylated oligosaccharide sequence that, in certain instances, is found on glycoconjugates. As used herein, an inhibitor of Neu5Ac($\alpha$2,6)Gal/GalNAc activity encompasses an inhibitor of the activity of oligosaccharides, glycoconjugates, glycoproteins, membrane-bound glycoproteins, and the like, which contain Neu5Ac($\alpha$2,6)Gal/GalNAc. In one embodiment, an inhibitor of Neu5Ac($\alpha$2,6)Gal/GalNAc activity directly inhibits the Neu5Ac($\alpha$2,6)Gal/GalNAc sequence. In another embodiment, an inhibitor of Neu5Ac($\alpha$2,6)Gal/GalNAc activity inhibits the entity (e.g., glycoconjugate, glycoprotein, etc.) that Neu5Ac($\alpha$2,6)Gal/GalNAc is attached.

In one embodiment, the composition comprises an inhibitor of sialyltransferase expression. For example, in one embodiment, the composition comprises an isolated nucleic acid (e.g., siRNA, ribozyme, antisense RNA, etc.) that reduces the expression level of sialyltransferase expression in a cell.

In one embodiment, the composition comprises an inhibitor of Neu5Ac($\alpha$2,6)Gal/GalNAc expression. For example, in one embodiment, the composition comprises an isolated nucleic acid (e.g., siRNA, ribozyme, antisense RNA, etc.) that reduces the expression level of Neu5Ac($\alpha$2,6)Gal/GalNAc expression in a cell.

In one embodiment, the composition comprises an inhibitor of sialyltransferase activity. For example, in one embodiment, the composition comprises a nucleic acid, peptide, small molecule, antagonist, aptamer, or peptidomimetic that reduces the activity of sialyltransferase. In one embodiment, the composition comprises the sialyltransferase inhibitor, cytidine, or analogs thereof.

In one embodiment, the composition comprises an inhibitor of the activity of Neu5Ac($\alpha$2,6)Gal/GalNAc. For example, in one embodiment, the composition comprises a nucleic acid, peptide, small molecule, antagonist, aptamer, or peptidomimetic that reduces the activity of Neu5Ac($\alpha$2,6)Gal/GalNAc. In one embodiment, the composition comprises 6'-sialyllactose (6'-SL), or analogs thereof. In one embodiment, the composition comprises 3'-sialyllactose (3'-SL), or analogs thereof.

In certain embodiments, the composition comprises a combination of inhibitors described herein. For example, in one embodiment the composition comprises a combination of at least two of cytidine, 6'-SL, and 3'-SL. In one embodiment, the composition comprises a botanical extract comprising an inhibitor of sialyltransferase and/or Neu5Ac($\alpha$2,6)Gal/GalNAc.

In one embodiment, the composition comprises a pharmaceutically acceptable carrier. For example, in certain embodiments, the composition comprises a vehicle for delivery of an inhibitor described herein. In one embodiment, the pharmaceutically acceptable carrier comprises a dermatologically acceptable vehicle.

In one embodiment, the present invention provides a method for treating or preventing hyperpigmentation. In certain embodiments, the method treats or prevents hyperpigmentation caused by melasma, post-inflammatory hyperpigmentation, or solar lentigenes (liver spots). In one embodiment, the method comprises administering to a subject an effective amount of a composition comprising an inhibitor of sialyltransferase activity, an inhibitor of Neu5Ac($\alpha$2,6)Gal/GalNAc activity, or a combination thereof. In certain embodiments, the method comprises administering the composition to a melanocyte of a subject.

In one embodiment, the present invention provides a method for reducing skin pigmentation. In one embodiment, the method comprises administering to a subject an effective amount of a composition comprises an inhibitor of sialyltransferase activity, an inhibitor of Neu5Ac($\alpha$2,6)Gal/Gal- NAc activity, or a combination thereof. In certain embodiments, the method comprises administering the composition to a melanocyte of a subject.

In one embodiment, the present invention provides a method of inhibiting the production of melanin. In one embodiment, the method comprises administering to a subject an effective amount of a composition comprises an inhibitor of sialyltransferase activity, an inhibitor of the activity of Neu5Ac(α2,6)Gal/GalNAc, or a combination thereof. In certain embodiments, the method comprises administering the composition to a melanocyte of a subject.

In one embodiment, the present invention provides a method of inhibiting the transfer of a melanosome from a melanocyte to a keratinocyte. In one embodiment, the method comprises administering to a subject an effective amount of a composition comprises an inhibitor of sialyltransferase activity, an inhibitor of the activity of Neu5Ac (α2,6)Gal/GalNAc, or a combination thereof. In certain embodiments, the method comprises administering the composition to a melanocyte of a subject.

Inhibitors

In one embodiment, the present invention provides a composition for reducing skin pigmentation in a subject, wherein the composition comprises an inhibitor of oligosaccharide formation. In one embodiment, the present invention provides a composition for reducing skin pigmentation in a subject, wherein the composition comprises an inhibitor of oligosaccharide activity. In one embodiment, the composition inhibits the formation and/or function of glycosylated oligosaccharides.

In one embodiment, the composition of the invention comprises an inhibitor of sialyltransferase activity. In one embodiment, a sialyltransferase inhibitor is an inhibitor of one or more members of the sialyltransferase family, including, but not limited to, members of the β-galactoside α2,3-sialyltransferase (ST3Gal) family, β-galactoside α2,6-sialyltransferase (ST6Gal) family, GalNAc α2,6-sialyltransferase (ST6GalNAc) family, and the α2,8-sialyltransferase (ST8Sia) family. In one embodiment, the sialyltransferase inhibitor is an inhibitor of ST3Gal. In one embodiment, the sialyltransferase inhibitor is an inhibitor of ST6Gal. In one embodiment, the sialyltransferase inhibitor is an inhibitor of ST6Gal.I. In one embodiment, an inhibitor of sialyltransferase activity is any compound, molecule, or agent that reduces, inhibits, or prevents the formation of Neu5Ac(α2, 6)Gal/GalNAc or Neu5Ac(α2,6)Gal/GalNAc-containing conjugates (e.g., oligosaccharides, glycoproteins, etc.). In one embodiment, an inhibitor of sialyltransferase activity comprises a nucleic acid, a peptide, a small molecule, a siRNA, a ribozyme, an antisense, an antagonist, an aptamer, a peptidomimetic, or any combination thereof.

In one embodiment, the composition of the invention comprises an inhibitor of Neu5Ac(α2,6)Gal/GalNAc. An inhibitor of Neu5Ac(α2,6)Gal/GalNAc activity is any compound, molecule, or agent that reduces, inhibits, or prevents the function of Neu5Ac(α2,6)Gal/GalNAc or Neu5Ac(α2, 6)Gal/GalNAc-containing conjugates (e.g., oligosaccharides, glycoproteins, etc.). In one embodiment, an inhibitor of Neu5Ac(α2,6)Gal/GalNAc is any compound, molecule, or agent that reduces, inhibits, or prevents melanin formation. In one embodiment, an inhibitor of Neu5Ac(α2,6)Gal/GalNAc is any compound, molecule, or agent that reduces, inhibits, or prevents melanosome transfer from a melanocyte to a keratinocyte. In one embodiment, an inhibitor of Neu5Ac(α2,6)Gal/GalNAc activity is a nucleic acid, a peptide, a small molecule, a siRNA, a ribozyme, an antisense, an antagonist, an aptamer, a peptidomimetic, or any combination thereof.

Small Molecule

When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery versus biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

There are more than 20 sialyltransferases in humans (Harduin-Lepers et al., 2001, Biochimie 83:727-37) and a number of sialyltransferase inhibitors have been reported (Lin et al., 2005, Biochem Biophys Res Commun, 331: 953-957; Izumi et al., 2005, J Org Chem, 70: 8817-8824; Chang et al., 2006, Chem Commun, 14: 629-931; Chang et al., 2006, Biochem Biophys Res Commun, 341: 614-619; Hsu et al., 2005, 96: 415-422; Kleineidam et al., 1997, Glycoconj J, 14: 57-66; Xia et al., 2006, J Org Chem, 71: 3696-3706; Lee et al., 2002, J Biol Chem, 277: 49341-49351; Gouyer et al., 2001, Front Biosci, 6: D1235-1244; Azuma et al., 2000, Glycoconj J, 17: 301-306; Delannoy et al., Glycoconj J. 1996, 13: 717-726; Kajihara et al., 1993, Carbohydr Res, 247: 179-193; Cambron and Leskawa, 1993, Biochem Biophys Res Commun, 193: 585-590; Kilton and Maca, 1977, J Natl Cancer Inst., 58: 1479-1481; Kijima-Suda et al., 1988, Cancer Res, 48: 3728-3732; Hindenburg et al., 1985, Cancer Res, 45: 3048-3052; Guette et al., 1983, Biochimie, 563-567; Shibuya et al., 1987, 262: 1596-1601; Wang et al., 2003, Bioorg Med Chem, 11: 4217-4224). In one embodiment, the sialyltransferase inhibitor is an inhibitor of ST6Gal.I. ST6Gal.I catalyzes formation of Neu5Ac(α2,6)Gal/GalNAc terminus of some N- and O-linked oligosaccharides and glycolipids (gangliosides). Exemplary sialyltransferase inhibitors include, but are not limited to, inhibitors listed in Table 1. In one embodiment, the composition comprises at least one of these sialyltransferase inhibitors, or additional such inhibitors not listed herein (Table 1).

TABLE 1

Inhibitors of sialyltransferase activity.

| | |
|---|---|
| Stachybotrydial | (Lin et al., 2005) |
| Cytidinyl-5-sialylethylphosphonate | (Izumi et aL, 2005) |
| Lithocholic acid analogs | (Chang et al., 2006a) |
| Soyasaponin I | (Hsu et al, 2005; Chang et. al., 2006b) |
| Cytidine | (Kleineidam et al., 1997) |
| 2-thiocytidine | (Kleineldam et al., 1997) |
| 5'-CDP | (Kleineidam et al., 1997) |
| 5'-CMP | (Kleineidam et al., 1997) |
| 5'-CTP | (Kleineidam et al., 1997) |
| fluorinated mucin core 2 branched oligosaccharides | (Xia et al., 2006) |
| Hexapeptide (NH(2)-GNWWWW) | (Lee et al., 2002) |
| GalNAcalpha-O-bn | (Guyer et al, 2001) |
| Etoposide | (Azuma et al., 2000) |
| acetyl-alpha-D-galactosaminide | (Delannoy et al., 1996) |
| 6'-modified methyl N-acetyl-beta-lactosaminide (6'-Deoxy, 6'-thio, and 6'-O-tetrahydropyranosyl analogues of methyl N-acetyl-beta-lactosaminide) and disulfide dimmers thereof | (Kajihara et al, 1993) |
| UDP-dialdehyde | (Cambron and Leskawa, 1993) |
| CMP-dialdehyde | (Cambron and Leskawa, 1993) |
| UDP | (Cambron and Leskawa, 1993) |
| CMP | (Kilton et al, 1977; Cambron and Leskawa, 1993) |
| UDP-Gal | (Cambron and Leskawa, 1993) |
| UDP-GalNAc | (Cambron and Leskawa, 1993) |
| UMP | (Kilton et al, 1977) |
| AMP | (Kilton et al, 1977) |
| GMP | (Kilton et al, 1977) |
| 5-fluoro-2',3'-isopropylidene-5'-O-(4-N-acetyl-2,4-dideoxy-3,6,7,8-tetra-O-acetyl-1-methoxycarbonyl-D-glycero-alpha-D-galactooctapyranosyl)uridine | (Kijima-Suda et al, 1988) |
| 3-Deazauridine | (Hindenburg et al., 1985) |
| Acivicin | (Hindenburg et al., 1985) |
| 1-beta-D-Arabinofuranosylcytosine | (Hindenburg et al., 1985) |
| Hydroxyurea | (Hindenburg et al.,1985) |
| bis-(p-nitroplienyl)phosphate | (Guette et al.,1983) |
| other | (Shibuya et al.1987; Wang et al, 2003) |

In one embodiment, the composition comprises cytidine. As described elsewhere herein, cytidine is found to reduce melanin formation and prevent melanosome transfer from melanocytes to keratinocytes. Thus, in one embodiment, the composition of the invention comprises cytidine, or analogs thereof, for the reduction of skin pigmentation. Examples of cytidine analogues include, but are not limited to, gemcitabine, deoxycytidine, 5-aza-2'-deoxycytidine (Decitabine or 5-aza-CdR), 1-β-D-arabinofuranosylcytosine (Cytarabine or ara-C), pseudoisocytidine (psi ICR); 5-fluoro-2'-deoxycytidine (FCdR), 5-aza-2'-deoxy-2',2'-difluorocytidine; 5-aza-2'-deoxy-2'-fluorocytidine, 1-β-D-ribofuranosyl-2(1H)-pyrimidinone (Zebularine), 2',3'-dideoxy-5-fluoro-3'-thiacytidine (Emtriva), 2'-cyclocytidine (Ancitabine), 1-β-D-arabinofuranosyl-5-azacytosine (Fazarabine or ara-AC), 6-azacytidine (6-aza-CR), 5,6-dihydro-5-azacytidine (dH-aza-CR), $N^4$-pentyloxycarbonyl-5'-deoxy-5-fluorocytidine (Capecitabine), $N^4$-octadecyl-cytarabine, and elaidic acid cytarabine.

In one embodiment, an inhibitor of Neu5Ac(α2,6)Gal/GalNAc comprises an oligosaccharide inhibitor. Previous studies reported a number of small oligosaccharides that showed inhibition of EBL-mediated precipitation of glycophorin, a highly sialylated glycoprotein, and deduced that the EBL lectin showed strong affinity for oligosaccharides containing the Neu5Ac(α2,6)Gal/GalNAc sequence (Shibuya et al, 1987, J Biol Chem, 262(4): 1596-1601). Non-limiting examples of such inhibitors shown in Table 2. In one embodiment, the composition of the invention comprises at least one of the inhibitors listed in Table 2, or analogs thereof, or similar structures not listed therein.

TABLE 2

Oligosaccharide inhibitors of Neu5Ac(α2,6)Gal/GalNAc

| | |
|---|---|
| p-Nitrophenyl N-aectyl-β-D-galactosaminide | (Shibuya et al., 1987) |
| Neu5Ac(α2-6)Gal(β1-4)Glc | (Shibuya et al., 1987) |
| Neu5Ac(α2-6)Gal(β1-4)Glc-ol | (Shibuya et al., 1987) |
| Neu5Ac(α2-6)Gal(β1-4)GlcNAc(β1-3)Gal(β1-4)Glc | (Shibuya et al., 1987) |
| Neu5Ac(α2-3)Gal(β1-3)GlcNAc(β1-3)Gal(β1-4)Glc | (Shibuya et al., 1987) |
| Bovine fetuin triantennary carbohydrate chains | (Shibuya et al., 1987) |
| Porcine thyroglobulin biantennary carbohydrate chains | (Shibuya et al., 1987) |

In one embodiment, the composition comprises 6'-sialyllactose (6'-SL) (Neu5Ac(α2,6)Gal(β1-4)Glc). In one embodiment, the composition comprises 3'-sialyllactose (3'-SL) (Neu5Ac(α2,3)Gal(β1-4)Glc). As described elsewhere herein, both 6'-SL and 3'-SL were found to reduce melanin formation and prevent melanosome transfer from melanocytes to keratinocytes. The discovery of 3'-SL as an inhibitor of Neu5Ac(α2,6)Gal/GalNAc was particularly surprising, as 3'-SL was previously found to not inhibit the staining of Neu5Ac(α2,6)Gal/GalNAc by EBL/SMA, as described elsewhere herein. Thus, in one embodiment, the composition of the invention comprises at least one of 6'-SL, or analogs thereof, and 3'-SL, or analogs thereof for the reduction of skin pigmentation.

In one embodiment, the small molecule inhibitor of the invention comprises at least one inhibitor listed in Table 1, or at least one inhibitor listed in Table 2, or at least one of cytidine, cytidine monophosphate N-acetylneuraminic acid, 6'-sialylgalactose, 6'-sialyl N-acetylgalactosamine, 6'-sialyllactose, 3'-sialyllactose, or N-acyl-neuraminyl. In one embodiment, the small molecule inhibitor of the invention comprises an analog or derivative of an inhibitor described herein.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog", "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to reduce skin pigmentation.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acids

In other related aspects, the invention includes an isolated nucleic acid encoding an inhibitor. In some instances the inhibitor is an siRNA or antisense molecule, which inhibits sialyltransferase and/or Neu5Ac($\alpha$2,6)Gal/GalNAc. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein. In another aspect of the invention, sialyltransferase and/or Neu5Ac($\alpha$2, 6)Gal/GalNAc, can be inhibited by way of inactivating and/or sequestering sialyltransferase and/or Neu5Ac($\alpha$2,6) Gal/GalNAc. As such, inhibiting the activity of sialyltransferase and/or Neu5Ac($\alpha$2,6)Gal/GalNAc can be accomplished by using a transdominant negative mutant.

In one embodiment, siRNA is used to decrease the level of sialyltransferase protein or decrease the level of proteins containing the Neu5Ac($\alpha$2,6)Gal/GalNAc sequence. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al.

(2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of sialyltransferase protein and/or Neu5Ac($\alpha$2,6)Gal/GalNAc-containing protein using RNAi technology.

In another aspect, the invention includes a vector comprising an siRNA or antisense polynucleotide. Preferably, the siRNA or antisense polynucleotide is capable of inhibiting the expression of a target polypeptide, wherein the target polypeptide is selected from the group consisting of sialyltransferase and Neu5Ac($\alpha$2,6)Gal/GalNAc-containing peptides. The incorporation of a desired polynucleotide into a vector and the choice of vectors is well-known in the art as described in, for example, Sambrook et al., supra, and Ausubel et al., supra, and elsewhere herein.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., "Molecular cloning, a Laboratory Manual", 2nd ed., Cold Spring Harbor Laboratory Press, N. Y., 1989 Vol 1-3]. In a particular embodiment, the vector is a vector useful for transforming animal cells.

In one embodiment, the recombinant expression vectors may also contain nucleic acid molecules which encode a peptide or peptidomimetic inhibitor of invention, described elsewhere herein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue (e.g., skin) Tissue specific promoters are well known in the art and include, but are not limited to, the keratin 14 promoter and the fascin promoter sequences.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence which is expressed by a plasmid vector is used to inhibit sialyltransferase and/or Neu5Ac($\alpha$2,6)Gal/GalNAc-containing protein expression. The antisense expressing vector is used to transfect a mammalian cell or the mammal itself, thereby causing reduced endogenous expression of sialyltransferase and/or Neu5Ac(α2,6)Gal/GalNAc-containing protein.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit sialyltransferase and/or Neu5Ac(α2,6)Gal/GalNAc-containing protein expression. Ribozymes useful for inhibiting the expression of a target molecule may be designed by incorporating target sequences into the basic ribozyme structure which are complementary, for example, to the mRNA sequence of sialyltransferase and/or Neu5Ac(α2,6)Gal/GalNAc-containing protein of the present invention. Ribozymes targeting sialyltransferase and/or Neu5Ac(α2,6)Gal/GalNAc-containing protein thereof, may be synthesized using commercially available reagents (Applied Biosystems, Inc., Foster City, Calif.) or they may be genetically expressed from DNA encoding them.

Polypeptides

In other related aspects, the invention includes an isolated peptide inhibitor that inhibits the activity of sialyltransferase and/or Neu5Ac(α2,6)Gal/GalNAc. For example, in one embodiment, the peptide inhibitor of the invention inhibits the activity of sialyltransferase and/or Neu5Ac(α2,6)Gal/GalNAc directly by binding to sialyltransferase and/or Neu5Ac(α2,6)Gal/GalNAc thereby preventing the normal functional activity of sialyltransferase and/or Neu5Ac(α2,6)Gal/GalNAc. In another embodiment, the peptide inhibitor of the invention inhibits the activity of sialyltransferase and/or Neu5Ac(α2,6)Gal/GalNAc by competing with endogenous sialyltransferase and/or Neu5Ac(α2,6)Gal/GalNAc. In yet another embodiment, the peptide inhibitor of the invention inhibits the activity of sialyltransferase and/or Neu5Ac(α2,6)Gal/GalNAc by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

A peptide inhibitor of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide inhibitor.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In a particular embodiment of the invention, the polypeptide of the invention further comprises the amino acid sequence of a tag. The tag includes but is not limited to: polyhistidine tags (His-tags) (for example H6 and H10, etc.) or other tags for use in IMAC systems, for example, $Ni^{2+}$ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the protein of the invention.

(b) Leader and Secretory Sequences

Accordingly, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest.

(c) Targeting Sequences

The invention also relates to a chimeric peptide comprising a peptide inhibitor described herein, fused to a targeting domain capable of directing the chimeric peptide to a desired cellular component or cell type or tissue. The chimeric peptide may also contain additional amino acid sequences or domains. The chimeric peptide are recombinant in the sense that the various components are from different sources, and as such are not found together in nature (i.e., are heterologous).

The targeting domain can be a membrane spanning domain, a membrane binding domain, or a sequence directing the peptide to associate with for example vesicles or with the nucleus. The targeting domain can target a peptide inhibitor to a particular cell type or tissue. For example, the targeting domain can be a cell surface ligand or an antibody against cell surface antigens of a target tissue (e.g., skin or melanocyte). A targeting domain may target a peptide inhibitor to a cellular component.

(d) Intracellular Targeting

Combined with certain formulations, such peptides can be effective intracellular agents. However, in order to increase the efficacy of such peptides, the peptide inhibitor can be provided as a fusion or chimeric peptide comprising a second peptide which promotes "transcytosis", e.g., uptake of the peptide by epithelial cells. To illustrate, the peptide inhibitor of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the peptide inhibitor can be provided a fusion polypeptide with all or a portion of the antenopedia III protein.

To further illustrate, the peptide inhibitor can be provided as a chimeric peptide which includes a heterologous peptide sequence ("internalizing peptide") which drives the translocation of an extracellular form of a peptide inhibitor across a cell membrane in order to facilitate intracellular localization of the peptide inhibitor. In this regard, the therapeutic peptide inhibitor is one which is active intracellularly. The internalizing peptide, by itself, is capable of crossing a cellular membrane by, e.g., transcytosis, at a relatively high rate. The internalizing peptide is conjugated, e.g., as a fusion protein, to the peptide inhibitor. The resulting chimeric peptide is transported into cells at a higher rate relative to the activator polypeptide alone to thereby provide an means for enhancing its introduction into cells to which it is applied.

In one embodiment, the internalizing peptide is derived from the Drosophila antennapedia protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269:10444-10450; and Perez et al. (1992) J Cell Sci 102: 717-722. Recently, it has been demonstrated that fragments as small as 16 amino acids long of this protein are sufficient to drive internalization. See Derossi et al. (1996) J Biol Chem 271:18188-18193.

The present invention contemplates a peptide inhibitor as described herein, and at least a portion of the Antennapedia protein (or homolog thereof) sufficient to increase the transmembrane transport of the chimeric protein, relative to the peptide inhibitor, by a statistically significant amount.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell, 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject peptide inhibitor.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of the subject peptide inhibitor, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., Pseudomonas exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the peptide inhibitor, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

As described above, the internalizing and accessory peptides can each, independently, be added to the peptide inhibitor by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In certain instances, it may also be desirable to include a nuclear localization signal as part of the peptide inhibitor.

In the generation of fusion polypeptides including the subject peptide inhibitors, it may be necessary to include unstructured linkers in order to ensure proper folding of the various peptide domains. Many synthetic and natural linkers are known in the art and can be adapted for use in the present invention, including the $(Gly_3Ser)_4$ linker.

(e) Peptide Inhibitor Mimetics

In other embodiments, the subject peptide inhibitor therapeutics are peptidomimetics of the peptide inhibitors. Peptidomimetics are compounds based on, or derived from, peptides and proteins. The peptidomimetics of the present invention typically can be obtained by structural modification of a known peptide inhibitor sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptide inhibitors.

Moreover, as is apparent from the present disclosure, mimetopes of the subject peptide inhibitor can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in Peptides: Chemistry and Biology, G. R. Marshall ed., ESCOM Publisher: Leiden, Netherlands, 1988)

In addition to a variety of side chain replacements which can be carried out to generate the peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the peptide inhibitor. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

A peptide inhibitor, or chimeric protein, of the invention may be synthesized by conventional techniques. For example, the peptide inhibitors or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

N-terminal or C-terminal fusion proteins comprising a peptide inhibitor, or chimeric protein of the invention conjugated with other molecules may be prepared by fusing, through recombinant techniques, the N-terminal or C-terminal of the peptide inhibitor, or chimeric protein, and the sequence of a selected protein or selectable marker with a desired biological function. The resultant fusion proteins contain the peptide inhibitor, or chimeric protein fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Antibodies

The invention also contemplates an inhibitor of sialyltransferase and/or Neu5Ac($\alpha$2,6)Gal/GalNAc comprising an antibody, or antibody fragment, specific for a sialyltransferase and/or Neu5Ac($\alpha$2,6)Gal/GalNAc. The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain F.sub.V molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Prior to its use as an inhibitor, a peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Combinations

In one embodiment, the composition of the present invention comprises a combination of sialyltransferase and/or Neu5Ac($\alpha$2,6)Gal/GalNAc inhibitors described herein. For example, in one embodiment the composition comprises a sialyltransferase inhibitor and a Neu5Ac($\alpha$2,6)Gal/GalNAc inhibitor. In certain embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

A composition, comprising a combination of inhibitors, comprises individual inhibitors in any suitable ratio. For example, in one embodiment, the composition comprises a 1:1 ratio of two individual inhibitors. In another embodiment, the composition comprises a 1:1:1 ratio of three individual inhibitors. However, the combination is not limited to any particular ratio. Rather any ratio that is shown to be effective is encompassed.

In one embodiment, the composition of the invention comprises cytidine and 6'-SL. In another embodiment, the composition of the invention comprises cytidine and 3'-SL. In another embodiment, the composition of the invention comprises 6'-SL and 3'-SL. In another embodiment, the composition of the invention comprises cytidine, 6'-SL and 3'-SL. In certain embodiments, a composition comprising at least two of cytidine, 6'-SL, and 3'-SL displays synergism.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. In one embodiment, the carrier comprises a dermatologically acceptable vehicle.

Exemplary dermatologically acceptable vehicles are well known in the art, and can include, for example, water, butylene glycol, triethanolamine, methylparaben, glycerin, titanium dioxide, polyacrylamide, hydrolyzed jojoba esters, propylene glycol, laureth-7, cetearyl ethylhexanoate, silica, glyceryl stearate, betaine, cyclopentasiloxane, dimethicone, cyclohexasiloxane, ammonium acryloyldimethyltaurate, dimethyl isosorbide, PEG-8 dimethicone, maltodextrin, xanthan gum, sodium cocyl isethionate, stearic acid, cetyl alcohol, sodiummethyl cocoyl taurate, polysorbate 60, biosaccharide gum, PPG-5-Ceteth-20, $C_{12}$-$C_{15}$ alkyl benzoate, zinc oxide, octinoxate, tribehenin, ozokerite, cyclomethicone, methicone, polyglyceryl-4 isosterate, or combinations thereof (US Patent Application Publication No. US2010/0260695). However, the dermatologically acceptable vehicle of the present invention is not limited to any particular ingredients or formulations. Rather, the composition comprises any suitable dermatologically acceptable vehicle known in the art or discovered in the future.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, antioxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Methods of Inhibiting

Sialyltransferase and/or Neu5Ac(α2,6)Gal/GalNAc activity can be inhibited using any method known to the skilled artisan. Examples of methods that inhibit sialyltransferase and/or Neu5Ac(α2,6)Gal/GalNAc activity, include but are not limited to, inhibiting expression of an endogenous gene encoding sialyltransferase and/or Neu5Ac(α2,6)Gal/GalNAc-containing protein, decreasing expression of mRNA encoding sialyltransferase and/or Neu5Ac(α2,6)Gal/GalNAc-containing protein, and inhibiting the function, activity, or stability of sialyltransferase and/or Neu5Ac(α2,6)Gal/GalNAc. A sialyltransferase and/or Neu5Ac(α2,6)Gal/GalNAc inhibitor may therefore be a compound that decreases expression of a gene encoding sialyltransferase and/or Neu5Ac(α2,6)Gal/GalNAc-containing protein, decreases mRNA half-life, stability, or expression of a mRNA encoding sialyltransferase and/or Neu5Ac(α2,6)Gal/GalNAc-containing protein, or inhibits sialyltransferase and/or Neu5Ac(α2,6)Gal/GalNAc function, activity or stability. A sialyltransferase and/or Neu5Ac(α2,6)Gal/GalNAc may be any type of compound, including but not limited to, a peptide, a nucleic acid, an aptamer, a peptidometic, and a small molecule, or combinations thereof.

Sialyltransferase and/or Neu5Ac(α2,6)Gal/GalNAc inhibition may be accomplished either directly or indirectly. For example, sialyltransferase and/or Neu5Ac(α2,6)Gal/GalNAc may be directly inhibited by compounds or compositions that directly interact with sialyltransferase and/or Neu5Ac(α2,6)Gal/GalNAc, such as antibodies. Alternatively, sialyltransferase and/or Neu5Ac(α2,6)Gal/GalNAc may be inhibited indirectly by compounds or compositions that inhibit sialyltransferase and/or Neu5Ac(α2,6)Gal/GalNAc downstream effectors, or upstream regulators which up-regulate sialyltransferase and/or Neu5Ac(α2,6)Gal/GalNAc expression.

Decreasing expression of an endogenous gene includes providing a specific inhibitor of gene expression. Decreasing expression of mRNA or protein includes decreasing the half-life or stability of mRNA or decreasing expression of mRNA. Methods of decreasing expression of sialyltransferase and/or Neu5Ac(α2,6)Gal/GalNAc-containing proteins include, but are not limited to, methods that use an siRNA, a microRNA, an antisense nucleic acid, a ribozyme, an expression vector encoding a transdominant negative mutant, a peptide, a small molecule, and combinations thereof.

Assays for Identifying and Testing Candidate Inhibitors

Sialyltransferase and/or Neu5Ac(α2,6)Gal/GalNAc inhibitors can be identified by screening test compounds for their capacity to reduce or preclude gene expression, mRNA expression, or protein activity, function or stability in a cell.

Expression of sialyltransferase and/or Neu5Ac(α2,6)Gal/GalNAc may be detected at either the protein or nucleic acid level. The invention should not be limited to any one method of protein or nucleic acid detection method recited herein, but rather should encompass all known or heretofor unknown methods of detection as are, or become, known in the art.

In one embodiment, antibodies specific for sialyltransferase and/or Neu5Ac(α2,6)Gal/GalNAc-containing protein are used to detect protein expression in a sample, where the sample may be a cell, a culture solution, or a body sample. The method comprises contacting the sample with at least one antibody directed to a sialyltransferase and/or Neu5Ac(α2,6)Gal/GalNAc-containing protein to determine if the expression of the sialyltransferase and/or Neu5Ac(α2,6)Gal/GalNAc-containing protein in the sample. Expression levels of the protein may be quantified using techniques well known in the art, including but not limited to densitometry. One of skill in the art will recognize that the immunocytochemistry method described herein below is performed manually or in an automated fashion.

Techniques for detecting antibody binding are well known in the art. Antibody binding to a protein may be detected through the use of chemical reagents that generate a detectable signal that corresponds to the level of antibody binding and, accordingly, to the level of protein expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the protein. Enzymes of particular interest include horseradish peroxidase (HRP) and alkaline phosphatase (AP). Commercial antibody detection systems, such as, for example the Dako Envision+ system (Dako North America, Inc., Carpinteria, Calif.) and Mach 3 system (Biocare Medical, Walnut Creek, Calif.), may be used to practice the present invention.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the protein are immobilized onto a selected surface exhibiting protein affinity, such as a well in a polystyrene microtiter plate. Then, a test sample is added to the wells. After binding and washing to remove non-specifically bound immunocomplexes, the bound antibody may be detected. Detection is generally achieved by the addition of a second antibody specific for the protein that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the protein antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the protein is immobilized, involves the use of antibody competition in the detection. In this ELISA, labeled antibodies are added to the wells, allowed to bind to the protein, and detected by means of their label. The amount of marker antigen in an unknown sample is then determined by mixing the sample with the labeled antibodies before or during incubation with coated wells. The presence of protein antigen in the sample acts to reduce the amount of antibody available for binding to the well and thus reduces the ultimate signal.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as, but not limited to, BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immunecomplex can be detected with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

In other embodiments, the expression of sialyltransferase and/or Neu5Ac($\alpha$2,6)Gal/GalNAc-containing protein is detected at the nucleic acid level. Nucleic acid-based techniques for assessing expression are well known in the art and include, for example, determining the level of mRNA in a body sample. Many expression detection methods use isolated RNA. Any RNA isolation technique that does not select against the isolation of mRNA can be utilized for the purification of RNA from body samples (see, e.g., Ausubel, ed., 1999, Current Protocols in Molecular Biology (John Wiley & Sons, New York). Additionally, large numbers of tissue samples can readily be processed using techniques well known to those of skill in the art, such as, for example, the single-step RNA isolation process of Chomczynski, 1989, U.S. Pat. No. 4,843,155).

The term "probe" refers to any molecule that is capable of selectively binding to a specifically intended target biomolecule, for example, a nucleotide transcript or a protein. Probes can be synthesized by one of skill in the art, or derived from appropriate biological preparations. Probes may be specifically designed to be labeled with a detectable label. Examples of molecules that can be used as probes include, but are not limited to, RNA, DNA, proteins, antibodies, and organic molecules.

Isolated mRNA can be detected in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding sialyltransferase and/or Neu5Ac($\alpha$2,6)Gal/GalNAc-containing protein. Hybridization of an mRNA with the probe indicates that the target in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array (Santa Clara, Calif.). A skilled artisan can readily adapt known mRNA detection methods for use in detecting the level of mRNA encoding sialyltransferase and/or Neu5Ac (α2,6)Gal/GalNAc-containing protein.

An alternative method for determining the level of target mRNA in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189 193), self-sustained sequence replication (Guatelli, 1990, Proc. Natl. Acad. Sci. USA, 87:1874 1878), transcriptional amplification system (Kwoh, 1989, Proc. Natl. Acad. Sci. USA, 86:1173 1177), Q-Beta Replicase (Lizardi, 1988, Bio/Technology, 6:1197), rolling circle replication (Lizardi, U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, expression is assessed by quantitative fluorogenic RT-PCR (i.e., the TaqMan® System). Such methods typically use pairs of oligonucleotide primers that are specific for sialyltransferase and/or Neu5Ac (α2,6)Gal/GalNAc-containing protein. Methods for designing oligonucleotide primers specific for a known sequence are well known in the art.

Expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression may also comprise using nucleic acid probes in solution.

In another embodiment of the invention, an in vitro binding assay is used to determine binding affinity and dissociation kinetics of potential inhibitors for sialyltransferase and/or Neu5Ac(α2,6)Gal/GalNAc. Examples of in vitro binding assays are well known in the art. Standards may be used when testing new agents or compounds or when measuring the various parameters described herein. In addition, when measuring a parameter, measurement of a standard can include measuring parameters such as sialyltransferase and/or Neu5Ac(α2,6)Gal/GalNAc concentrations in a tissue or fluid obtained from a subject before the subject is treated with a test compound and the same parameters can be measured after treatment with the test compound. In another aspect of the invention, a standard can be an exogenously added standard which is an agent or compound that is added to a sample and is useful as an internal control, especially where a sample is processed through several steps or procedures and the amount of recovery of a marker of interest at each step must be determined. Such exogenously added internal standards are often added in a labeled form, i.e., a radioactive isotope.

Test compounds for use in such screening methods can be small molecules, nucleic acids including aptamers, peptides, peptidomimetics and other drugs. Fragments of sialyltransferase and/or Neu5Ac(α2,6)Gal/GalNAc are contemplated that can competitively inhibit the binding of sialyltransferase and/or Neu5Ac(α2,6)Gal/GalNAc to a sialyltransferase and/or Neu5Ac(α2,6)Gal/GalNAc binding partner, thereby inhibiting sialyltransferase and/or Neu5Ac(α2,6)Gal/GalNAc activity.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors of sialyltransferase and/or Neu5Ac(α2,6)Gal/GalNAc may be useful in therapeutic applications, or serve as lead drugs in the development of therapeutics. Synthetic techniques may be used to produce compounds, such as: chemical and enzymatic production of small molecules, peptides, nucleic acids, antibodies, and other therapeutic compositions useful in the practice of the methods of the invention. Other techniques may be used which are not described herein, but are known to those of skill in the art.

In one aspect of the invention libraries of small molecules, including but not limited to aptamers, peptidomimetics, fragments, or peptidomimetics, may be assayed for competitive binding to sialyltransferase and/or Neu5Ac(α2,6) Gal/GalNAc binding partners.

Inhibitors useful in the invention may be obtained using standard methods known to the skilled artisan. Such methods include chemical organic synthesis or biological means. Biological means include purification from a biological source, recombinant synthesis and in vitro translation systems, using methods well known in the art.

The invention also contemplates the agents (e.g., motifs, peptides comprising the motifs, and peptide mimetics thereof) identified using this method of the invention. The agents (e.g., motifs, peptides comprising the motifs, and peptide mimetics thereof) may be used to modulate sialyltransferase and/or Neu5Ac(α2,6)Gal/GalNAc degradation, and they may be used to modulate cellular processes of cells in which the agents are introduced. Accordingly, the agents (e.g., motifs, peptides comprising the motifs, and peptide mimetics thereof) may be formulated into compositions for administration to individuals suffering from a disease, disorder, or condition related to sialyltransferase and/or Neu5Ac(α2,6)Gal/GalNAc activity.

Treatment Methods

The present invention provides methods of reducing skin pigmentation comprising administering an effective amount of a composition comprising an inhibitor of oligosaccharide formation. In one embodiment, the present invention provides methods of reducing skin pigmentation comprising administering an effective amount of a composition comprising an inhibitor of sialyltransferase activity. In one embodiment, the present invention provides methods of reducing skin pigmentation comprising administering an effective amount of a composition comprising an inhibitor of oligosaccharide activity. In one embodiment, the composition inhibits the formation and/or function of glycosylated oligosaccharides.

The invention includes methods for the treatment of a sialyltransferase and/or Neu5Ac(α2,6)Gal/GalNAc related disorder. As used herein, the term "sialyltransferase and/or Neu5Ac(α2,6)Gal/GalNAc related disorder" refers to any disease, disorder, or condition which is caused or characterized by activity of sialyltransferase and/or Neu5Ac(α2,6)Gal/GalNAc. In one embodiment, the invention includes methods for the treatment of hyperpigmentation. In another embodiment, the invention includes methods for the treatment of excess pigmentation. In another embodiment, the invention includes methods for the treatment of uneven pigmentation. In another embodiment, the invention includes methods for reducing skin pigmentation.

Administration of a sialyltransferase and/or Neu5Ac(α2,6)Gal/GalNAc inhibitor in a method of treatment can be achieved in a number of different ways, using methods known in the art. For example, in certain embodiments, the method comprises topically administering a sialyltransferase and/or Neu5Ac(α2,6)Gal/GalNAc inhibitor to the skin of a subject. In certain embodiments, the method comprises a parenteral administration of a sialyltransferase and/or Neu5Ac(α2,6)Gal/GalNAc inhibitor.

The treatment and prophylactic methods of the invention may be used to reduce skin pigmentation in any subject in need. For example, in certain embodiments, the subject includes, but is not limited to humans and other primates and mammals including commercially relevant mammals such as non-human primates, cattle, pigs, horses, sheep, cats, and dogs.

It will be appreciated that a sialyltransferase and/or Neu5Ac(α2,6)Gal/GalNAc inhibitor of the invention may be administered to a subject either alone, or in conjunction with another therapeutic agent.

In one embodiment, an sialyltransferase and/or Neu5Ac (α2,6)Gal/GalNAc inhibitor is administered to a subject. The inhibitor may also be a hybrid or fusion composition to facilitate, for instance, delivery to target cells or efficacy. In one embodiment, a hybrid composition may comprise a tissue-specific targeting sequence. For example, in one embodiment, the inhibitor is targeted to a melanocyte or a dendrite of a melanocyte.

The therapeutic and prophylactic methods of the invention thus encompass the use of pharmaceutical compositions comprising a sialyltransferase and/or Neu5Ac(α2,6)Gal/GalNAc inhibitor to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In a preferred embodiment, the invention includes methods for treating hyperpigmentation by inhibiting the activity of sialyltransferase and/or Neu5Ac(α2,6)Gal/GalNAc. In one aspect, sialyltransferase and/or Neu5Ac(α2,6)Gal/GalNAc activity is inhibited by administering a sialyltransferase and/or Neu5Ac(α2,6)Gal/GalNAc inhibitor to a subject in order to inhibit melanin production or melanosome transfer.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. In another embodiment, the method comprises administering three individual inhibitors at a 1:1:1 ratio. However, the method is not limited to any particular ratio. Rather any ratio that is shown to be effective is encompassed.

In one embodiment, the method comprises administering cytidine and 6'-SL. In another embodiment, the method comprises administering cytidine and 3'-SL. In another embodiment, the method comprises administering 6'-SL and 3'-SL. In another embodiment, the method comprises administering cytidine, 6'-SL and 3'-SL. In certain embodiments, a method comprises administering at least two of cytidine, 6'-SL, and 3'-SL displays synergism.

In certain embodiments, the method comprises administering a composition comprising a combination of inhibitors. For example, in one embodiment the method comprises administering a composition comprising cytidine and 6'-SL. In one embodiment, the method comprises administering a composition comprising cytidine and 3'-SL. In another embodiment, the method comprises administering composition comprising 6'-SL and 3'-SL. In another embodiment, the method comprises administering a composition comprising cytidine, 6'-SL and 3'-SL.

In certain embodiments, the method comprises administering one or more compositions, where each composition comprises one or more inhibitors. For example, in one embodiment, the method comprises administering a first composition comprising cytidine and a second composition comprising 6'-SL. In one embodiment, the method comprises administering a first composition comprising cytidine and a second composition comprising 3'-SL. In one embodiment, the method comprises administering a first composition comprising 6'-SL and a second composition comprising 3'-SL. In one embodiment, the method comprises administering a first composition comprising cytidine, a second composition comprising 6'-SL, and a third composition comprising 3'-SL. The different compositions may be administered to the subject in any order and in any suitable interval. For example, in certain embodiments, the one or more compositions are administered simultaneously or near simultaneously. In certain embodiments, the method comprises a staggered administration of the one or more compositions, where a first composition is administered and a second composition administered at some later time point. Any suitable interval of administration which produces the desired therapeutic effect may be used.

The administration of a nucleic acid or peptide inhibitor of the invention to the subject may be accomplished using gene therapy. Gene therapy is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. Preferably the cell is a cell of the germinal line, an embryonic cell or egg cell or derived from the same, more preferably the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

Kits of the Invention

In one embodiment, the invention is a kit comprising a composition and instructional material for use thereof. In one embodiment, the composition comprises one or more inhibitors, as described elsewhere herein. In one embodiment, the kit comprises a plurality of compositions, where one or more of the plurality of compositions comprises one or more of inhibitors. In some embodiments, the kit comprises an applicator. The instructional material included in the kit includes instructions for the use of the inhibitor composition. In various embodiments, the instructional material recites, in whole or in part, the type of inhibitor in the composition, the amount of the inhibitor composition to be used, the frequency of its administration, the results to be achieved by the administration of the inhibitor composition, as well as other parameters for the use of inhibitor composition.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Role of Neu5Ac(α2,6)Gal/GalNAc on Melanin Content and Melanosome Transfer

As humans we are social beings where uneven or asymmetric pigmentation on the face and other areas of the body can cause lowered self-esteem, depression, problems with social status and reduced productivity in the workplace (Balkrishnan et al, 2006, Int J Dermatol 45:111-5). Hyperpigmentation of the skin is a common condition for which many individuals seek corrective treatment. It is the result of increased cutaneous melanin, sometimes asymmetrically in a spot or covering particular regions of skin; in other cases with bilateral symmetry. This can be caused by increased melanin synthesis and transfer to keratinocytes; a greater number of melanocytes; and in some cases by melanophages, melanin-containing macrophages that accumulate melanin through phagocytosis. Hyperpigmented regions are brown to blue-grey. There are many causes of hyperpigmentation, some of the most common being melasma, post-inflammatory hyperpigmentation (PIH) and solar lentigenes (liver spots). Accordingly, the inventions herein focus on new compounds and combinations thereof for reducing excess and uneven skin pigmentation. The compounds target specific glycosylation pathways for melanogenesis and transfer of melanosomes from melanocytes to keratinocytes.

It has been demonstrated herein that glycosylation has a role in melanin/melanosome synthesis and cell-cell transfer. Excess or uneven skin pigmentation can cause severe anxiety and depression in affected individuals. Several topical treatments to reduce hyperpigmentation are available commercially, however none has yet proved to be fully satisfactory. This invention concerns compounds and methods to reduce skin pigmentation through inhibition of the synthesis and function of oligosaccharides regulating the pigmentary system. The oligosaccharides to be expressed by melanocyte dendrites have been identified herein. As such they are closely associated with the transfer of melanosomes to keratinocytes, a rate-limiting step in skin pigmentation. Thus, inhibitors of melanin transfer described herein would be useful for skin pigment reduction in areas of hyperpigmentation such as in melasma, post-inflammatory hyperpigmentation, and solar lentigenes ("liver spots"), and in general to achieve a more even skin tone.

The materials and methods employed in these experiments are described.

Cell Culture

Primary neonatal normal human keratinocytes (NHKs) (Invitrogen, Life Technologies, Grand Island, N.Y.) were seeded at a density of $5 \times 10^5$ cells/well into 4-well collagen coated chamber slides (Fisher Scientific, Waltham, Mass.). Cells were maintained in 1 ml of serum-free keratinocyte growth medium (KGM) (Keratinocyte-SFM, Invitrogen) and incubated for 48 h in 5% $CO_2$ incubator. The complete KGM was prepared by adding KGM Singlequots (Lonza). Darkly pigmented human neonatal epidermal melanocytes (HEM-DP) (Invitrogen) were seeded over keratinocytes at $2.5 \times 10^5$ cells/well and incubated for 24 h at 37° C. The KGM was replaced with 1 ml of melanocyte growth medium (MGM) (Invitrogen), and the co-cultures were incubated for another 48 hours. The co-cultures were treated with the inhibitors at indicated concentrations in a final volume of 20 microliter/well in triplicate for 72 h. The cells were gently washed with 1× phosphate buffered saline (PBS) and fixed in 4% Paraformaldehyde (PFA) for 20 minutes at room temperature.

Lectin Histochemistry

Cells fixed in 4% PFA were washed in 1×PBS and incubated for 10 minutes at room temperature in dual enzyme block solution (Dako, Glostrop, Denmark) followed by wash in 1×PBS, and then incubated with protein block solution for 10 minutes at room temperature. The cells were then incubated with biotinylated elderberry bark lectin (1:800) (Vector Labs, Burlingame, Calif.) for 30 minutes at room temperature. Following a wash in 1×PBS, the cells were incubated with vectastain ABC-AP (Vector Labs) complex for 30 minutes at room temperature. The ABC-AP complex was prepared fresh according to the instructions provided with the vectastain ABC-AP kit. The cells were washed in 1×PBS to remove the ABC-AP complex and incubated with fast red chromagen staining solution (Dako) for 10 minutes at room temperature. The cells were rinsed in water and incubated with gill free hematoxylin for 5 minutes. The slides were rinsed in $H_2O$ followed by a gentle wash with 0.5% ammonium hydroxide. The slides were air dried and mounted on cover slips and the images were captured in tiff format using fluorescence microscope (Nikon) and analyzed.

Fontana-Masson Silver Stain for Melanin

Silver staining for melanin was performed according to the instructions provided with the Fontana-Masson staining kit (American MasterTech, Lodi, Calif.). Cells grown in collagen-coated chamber slides were fixed in 4% PFA and rinsed with water for 5 minutes to remove traces of PBS. Slides were then placed in ammonical silver solution followed by incubation in solutions of 0.1% gold chloride, 5% sodium thiosulfate, rinsed in running tap water to remove the staining solution, and dehydrated through 3 changes of fresh absolute alcohol. Cleared slides were rinsed through 3 changes of fresh xylene and coverslips were applied with mounting medium.

Treatment with Inhibitors

Cells were plated on 24-well plates at $2×10^5$ cells/well and treated with various inhibitors in triplicate. Media were replaced with fresh inhibitor-containing media every 24 h. After 72 h, cells were lysed with cell lysis buffer (Invitrogen) containing protease inhibitor cocktail and PMSF (phenylmethyl sulfonyl fluoride) and incubated for 20 minutes on ice. Following incubation with the lysis buffer, the lysed cells were centrifuged at 10,000 rpm for 10 minutes. From the same samples, the supernatants were saved for measurement of dopa oxidase activity and the pellets were evaluated for melanin content.

Dopa Oxidase Assay

Reaction mixture contained 20 µl of the lysate supernatant, 20 µl of 10 mM L-Dopa in 160 µl of 50 mM sodium phosphate buffer (0.1 M, pH6.8) Samples in triplicate sample were transferred to 96-well plates and immediately evaluated for the formation of dopachrome by reading the absorbance at 475 nm for 30 minutes at 1 minute intervals on M5 microplate reader (ThermoScientific, Waltham, Mass.). The slope derived from the kinetics was used to calculate the % dopa oxidase/tyrosinase activity in treated wells relative to the untreated controls.

Melanin Assay

Melanin was extracted following a previously described procedure (Ni-Komatsu, et al., 2005, Pigment Cell Res 18(6),447-453). In brief, the growth medium was removed and the cells lysed as above. The lysed cells were centrifuged and the pellet was washed with ethanol:ether (1:1) solution and then solubilized in 100 µl 20% DMSO in 2N NaOH. The melaninextracts (100 µl) were transferred to a 96-well plate and total melanin content quantitated with a M5 Spectramax plate reader (490 nm).

Photography and Image Processing

Representative fields of cultured cells were photographed with a Zeiss Axioskop 40 light microscope equipped with a Spot Flex digital camera. Using Photoshop tools, areas of interest were cut and pasted into the treatment groups herein. For a given Figure, any composite images were enhanced together, in a single layer, with automatic contrast and brightening tools.

Statistics

Dose response curves were assessed for Bliss Additivity and synergism as described (Fitzgerald et al., 2006, Nat Chem Biol 2:458-466; Ritz, C. & Streibig, J. C. (2005) Bioassay Analysis using R. J. Statist. Software, Vol 12, Issue 5). For comparisons of melanin content and tyrosinase/dopa oxidase activity in treated vs. untreated cultures, P-values were determined by the Welch Two Sample t-test.

Knockdown of ST6 and ST3

Mouse melan-A cells were seeded at $8×10^4$ cells/well in a 24 well plate and incubated for 24 hrs at 37° C. They were then transfected with ST6 and ST3 siRNAs according to the RNAiFect Transfection Handbook (Qiagen). Briefly, 1 µg each of siRNA ST6 and siRNA ST3 was added to RNAi Fect transfection reagent at dilutions of 1:3 and 1:6; complexed with 3 µl and 6 µl of the RNAiFect in 100 µl of culture medium; incubated for 10-15 min with Melan-A cells at room temperature and then an additional 24 hr at 37° C. The cultures were rinsed, fresh culture medium was added and the cells were incubated an additional 24 hr at 37° C., after which they were fixed and stained with EBL (Ni-Komatsu et al., 2005, Pigment Cell Res, 18: 447-53).

The results of the experiments are now described.

Lectin Binding Studies in Cutaneous Biopsies

Figure 2:
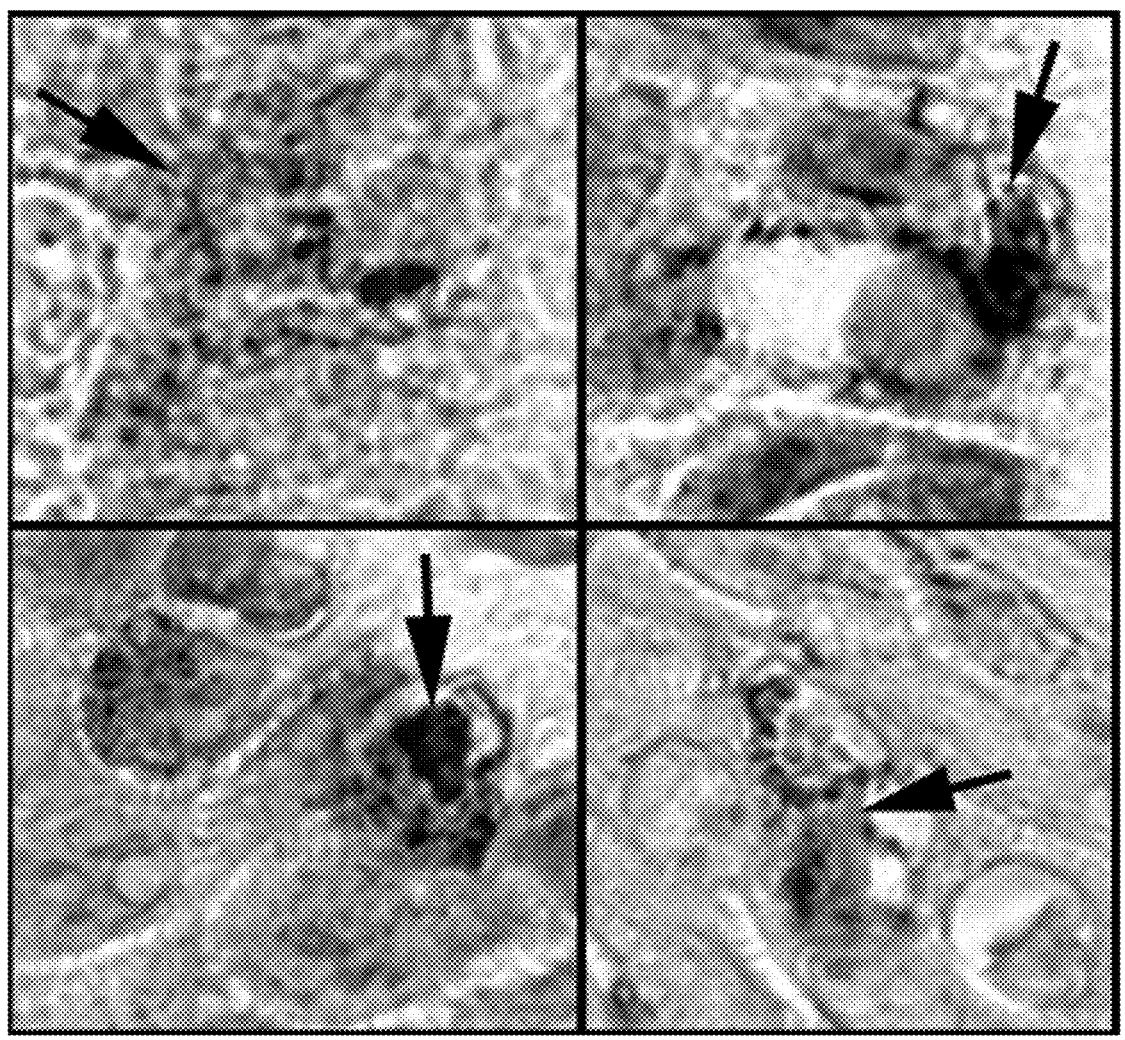
FIG. 2 is a set of images depicting the results of experiments illustrating the histochemical staining of melanocytes from 4 different individuals using elderberry bark lectin (EBL/SNA) as a marker. Sections were stained through standard immunoperoxidase methods using a brown chromagen. Counter-staining was with hematoxylin. The panels show single melanocytes surrounded by numerous keratinocytes. Arrows point to the nuclei of the melanocyte.

A panel of 20 biotinylated lectins was assembled as markers for specific glycosylation structures and used lectin histochemistry to analyze their staining patterns in skin biopsies with normal epidermal melanocytes and keratinocytes. While most of the 20 lectins studied showed no specific staining of melanocytes, the elderberry bark lectin, EBL/SNA, was notable because it stained normal melanocytes compared to other cells in the epidermis, with prominent labeling of dendrites. EBL/SNA recognizes the terminal Neu5Ac($\alpha$2,6)Gal/GalNAc sequence on certain glycans, Shown in FIG. 2 are light microscope photographs of biopsies stained with EBL and a brown chromagen. Each of the 4 panels is from a different individual. Staining reveals melanocytes in the basal layer of the epidermis with prominent melanocyte dendrites emanating from the cell body (FIG. 2). The melanocyte nuclei (marked by arrows) stain blue from the hematoxylin counterstain as do the surrounding keratinocytes. The same staining patterns were seen in biopsies from individuals of a variety of ethnic backgrounds and skin colors.

Figure 3:
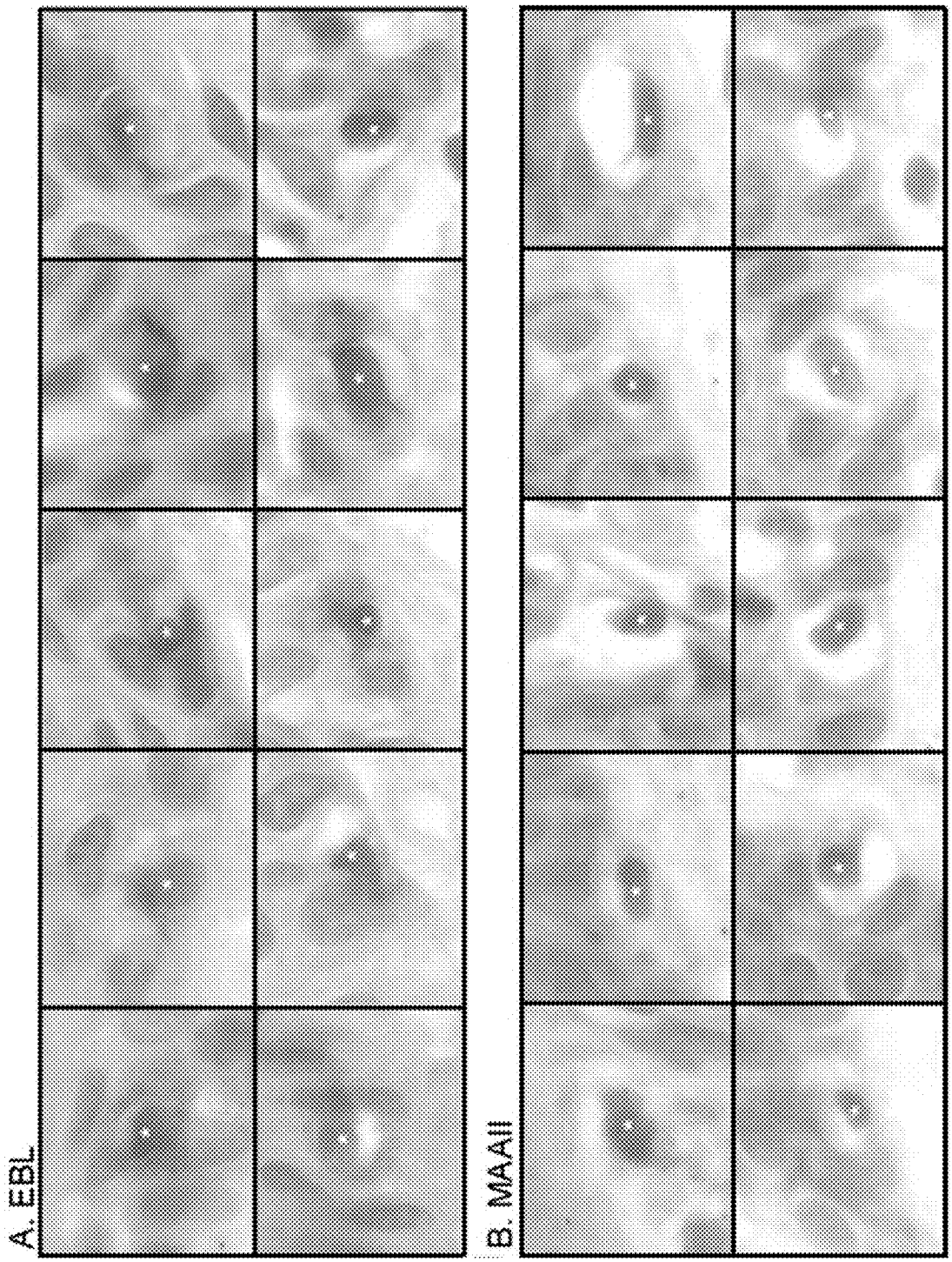
FIG. 3, comprising

In a second study, histological sections of skin biopsies from a single individual were stained with EBL and, as a control, the MAAII lectin (*Maackia amurensis* L.) that had shown little or no staining of melanocytes in the 20 lectin survey mentioned above (FIG. 3A and FIG. 3B). MAAII recognizes the Neu5Ac($\alpha$2,3)Gal/GalNAc sequence. As in FIG. 2, EBL staining marked prominent melanocyte dendrites emanating from the cell body (FIG. 3A). In contrast the MAAII lectin (*Maackia amurensis* L.) did not stain melanocytes (FIG. 3B). MAAII recognizes the Neu5Ac(α2, 3)Gal/GalNAc sequence. These findings serve to emphasize the specificity of the EBL lectin and the Neu5Ac(α2,6)Gal/GalNAc sequence for melanocytes.

EBL/SNA Binding in Melanocyte-Keratinocyte Co-Cultures

Figure 4:
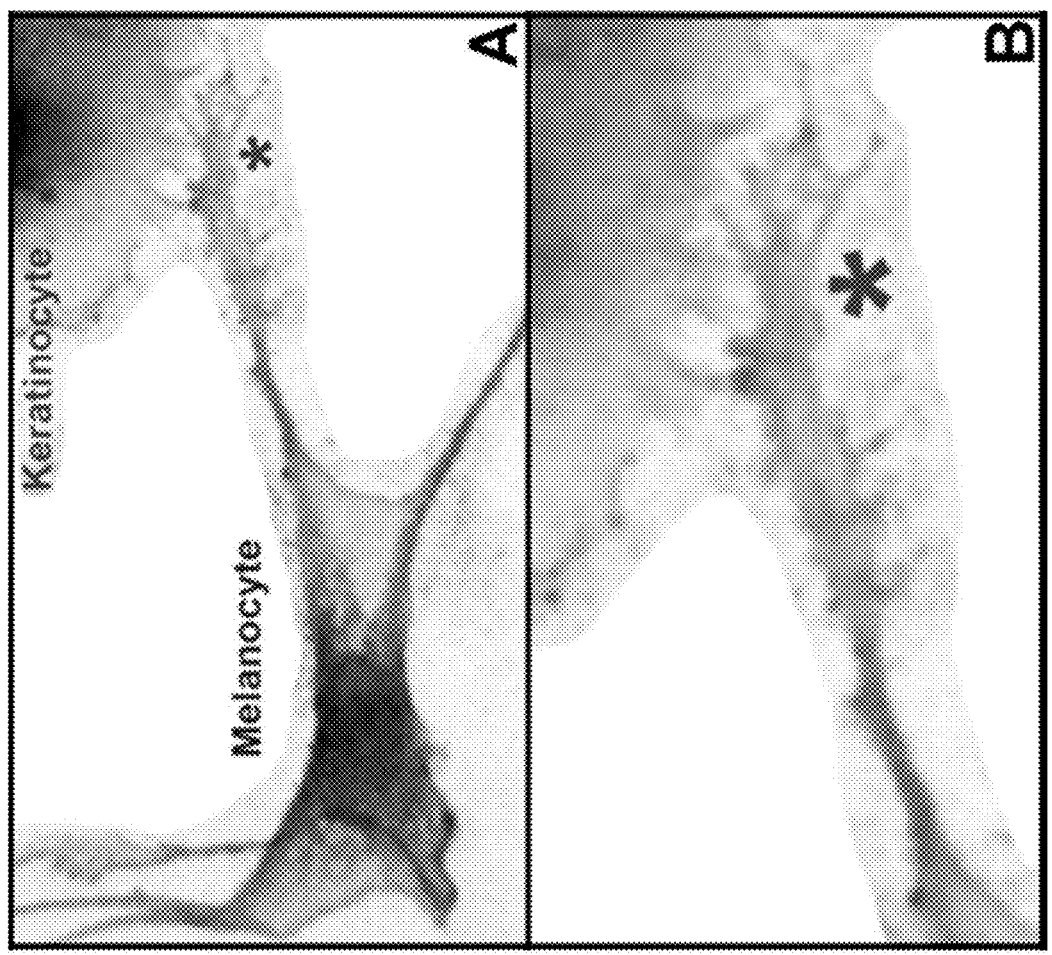
FIG. 4, comprising

EBL/SNA staining was next investigated in co-cultures of human melanocytes and keratinocytes. EBL/SNA staining was visualized with a red chromagen. FIG. 4A shows a melanocyte in contact with a keratinocyte. The melanocyte plasma membrane, including dendrites, stains strongly with EBL/SNA. At points of contact with the keratinocyte, the melanocyte dendrite extends numerous filapodia that also stain with EBL/SNA (asterisk). A higher power view is shown in FIG. 4B.

Specific Oligosaccharide Sequence Recognized by EBL/SNA

The sialylated oligosaccharide sequence, Neu5Ac(α2,6)Gal/GalNAc, recognized by EBL/SNA, is the terminal sequence for some membrane-associated glycoconjugates in various biological systems (Schauer, 2009, Curr Opin Struct Biol 19:507-514). Binding is highly specific, as the EBL discriminates between the Neu5Ac(α2,6)Gal/GalNAc sequence and the related Neu5Ac(α2,3)Gal/GalNAc sequence (recognized by MAAII) due to steric hindrance (Shibuya et al, 1987, J Biol Chem, 262(4): 1596-1601; Kaku et al, 2007, J Biochem, 142: 3). The results presented herein demonstrate for the first time that the Neu5Ac(alpha2,6)Gal/GalNAc sequence recognized by the EBL/SNA lectin is at the terminus of glycans on melanocyte dendrites where they are likely to be involved with melanosome transfer to keratinocytes. This would represent a previously unrecognized step in the pigmentation pathway. Consistent with this, N- and O-linked oligosaccharides with terminal neuraminic/sialic acid function in biological recognition systems, including cell-cell recognition and attachment (Schauer, 2009, Curr Opin Struct Biol 19:507-514). Since melanosome transfer to keratinocytes is a rate-limiting step in skin pigmentation, this suggests that disruption of Neu5Ac(α2, 6)Gal/GalNAc-oligosaccharide synthesis and/or function might inhibit melanosome transfer and thus provide a method for reducing skin pigmentation. Potential inhibitors of these processes were thus tested to determine how they might affect melanocytes and keratinocytes in co-culture.

Effects of L-Cytidine on EBL Binding in Melanocyte-Keratinocyte Co-Cultures

Figure 5:
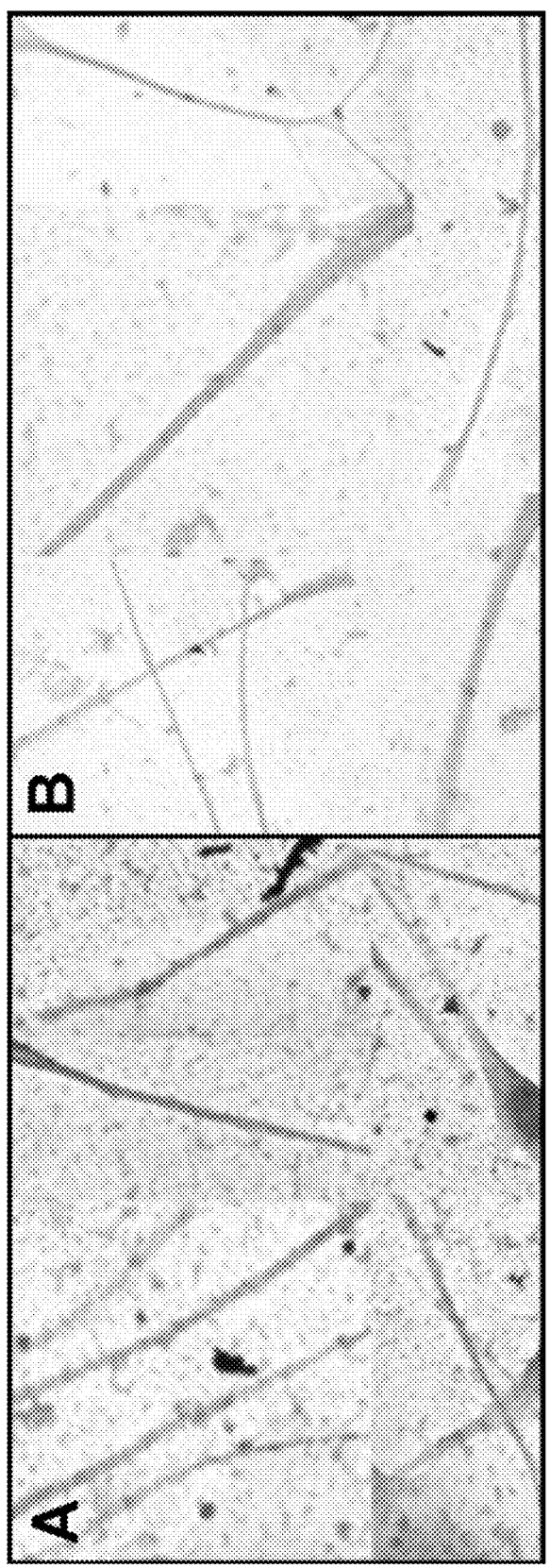
FIG. 5, comprising

Experiments were carried out to test the effects of cytidine, a ST6Gal.I inhibitor (Kleineidam et al., 1997, Glycoconj J, 14: 57-66), on the EBL/SNA staining in melanocyte-keratinocyte co-cultures (FIG. 5). Untreated cultures showed prominent EBL staining of melanocyte dendrites, including filapodia in contact with keratinocytes. This close association indicated that oligosaccharides terminated with Neu5Ac(α2,6)Gal/GalNAc function in melanosome transfer (FIG. 5A). Treatment with cytidine markedly reduced EBL staining (FIG. 5B). These results indicate that ST6Gal.I is necessary for Neu5Ac(α2,6)Gal/GalNAc-oligosaccharide formation and that cytidine is an effective inhibitor of this process.

Figure 6:
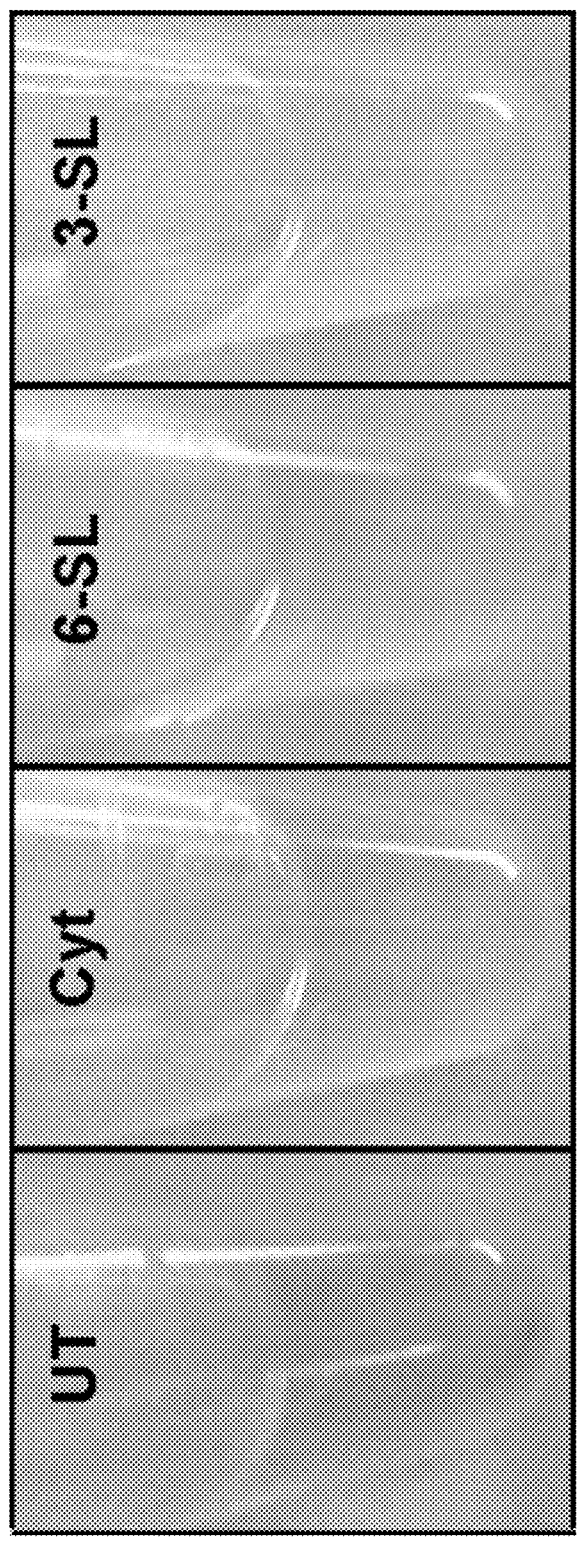
FIG. 6 is a set of images depicting the results of experiments demonstrating the effects of L-cytidine (Cyt, 50 micromolar), 6'-sialyllactose (6'-SL, 50 micromolar) and 3'-sialyllactose (3'-SL, 50 micromolar) on melanin content of human melanocyte-keratinocye co-cultures compared to an untreated control (UT). Cultures were incubated 72 hr with each agent, pelleted by centrifugation, and melanin was solubilized for quantitation via spectrophotometry. Original images were produced with a Zeiss Axioskop 40 light microscope equipped with a Spot Flex digital camera. All images were enhanced together with automatic contrast and brightening tools.

Effects of L-Cytidine, 6'-Sialyllactose and 3'-Sialyllactose on Melanin Content in Melanocyte-Keratinocyte Co-Cultures The effects of cytidine on melanin content were thus tested in human melanocyte-keratinocyte co-cultures. Also tested was 6'-sialyllactose (Neu5Ac(α2,6)Gal(β1-4)Glc; 6'-SL), an oligosaccharide homologue of the EBL/SNA recognition sequence and a strong inhibitor of EBL-mediated precipitation of glycophorin, a highly sialylated glycoprotein (Shibuya et al, 1987, J Biol Chem, 262(4): 1596-1601; Kaku et al, 2007, J Biochem, 142: 3). As a control, cultures were incubated with 3'-sialyllactose (Neu5Ac(α2, 6)Gal(β1-4)Glc; 3'-SL) which does not interact with the EBL/SNA binding site due to steric hindrance, and consequently is a poor inhibitor of EBL-mediated precipitation of glycophorin (Shibuya et al, 1987, J Biol Chem, 262(4): 1596-1601 Kaku et al, 2007, J Biochem, 142: 3). Cultures were incubated for 72 h with each agent, the cells were pelleted by centrifugation, and melanin was solubilized and quantitated through spectrophotometry. All three agents individually reduced melanin content compared to that in untreated cultures (FIG. 6). Unexpectedly, this included 3'-SL which gave the strongest reduction of the three. This was surprising since 3'-SL is a poor competitor for EBL binding, as discussed (Shibuya et al, 1987, J Biol Chem, 262(4): 1596-1601; Kaku et al, 2007, J Biochem, 142: 3).

Figure 7:
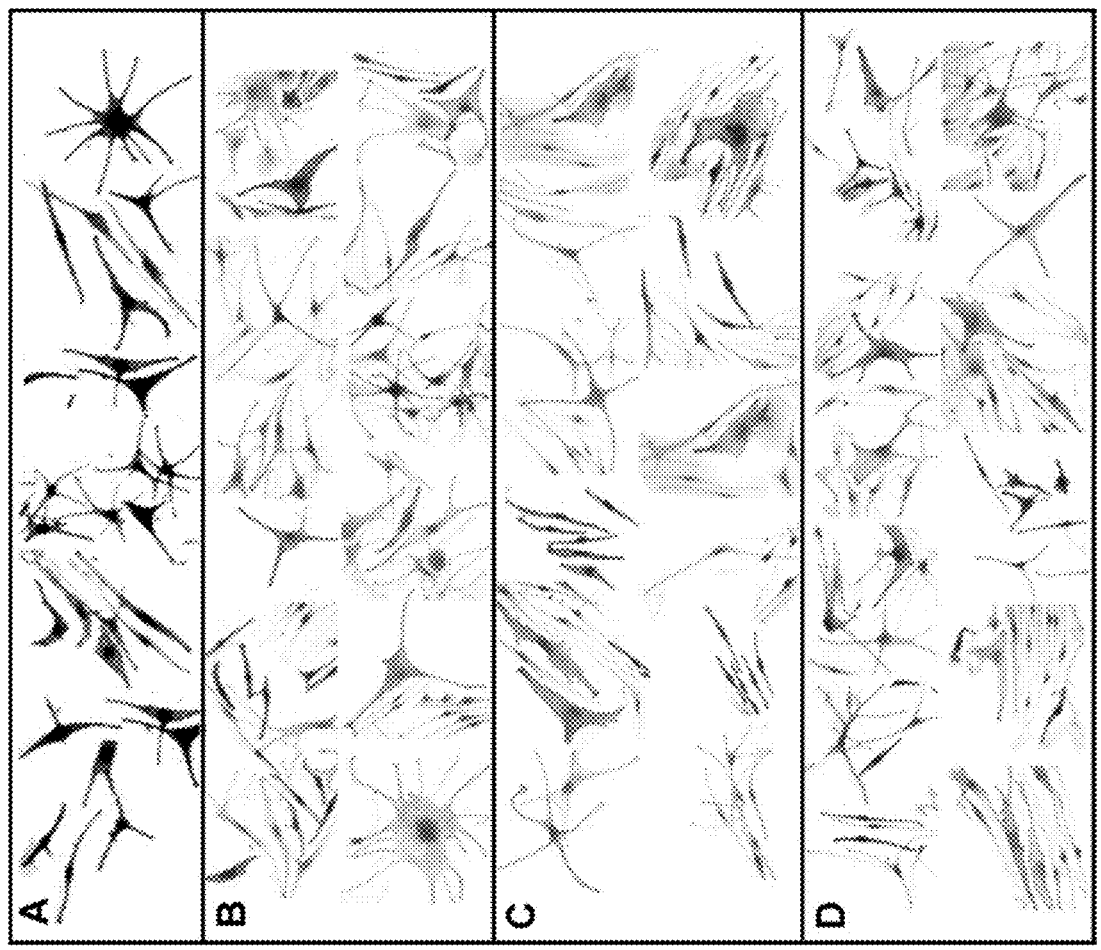
FIG. 7, comprising

Similarly, when melanocyte-keratinocyte co-cultures were stained for melanin with the Fontana-masson silver staining procedure (Kwon-Chung et al., 1981, J Clin Microbiol, 13383-387), cytidine, 6'-SL and 3'-SL each reduced melanin content in melanocytes-keratinocyte co-cultures (FIG. 7). This indicated that melanogenesis within melanocytes and transfer of melanosomes into keratinocytes were each inhibited by these agents.

Effects of 6'-SL and 3'-SL in Combination with Cytidine on Melanogenesis

Figure 8:
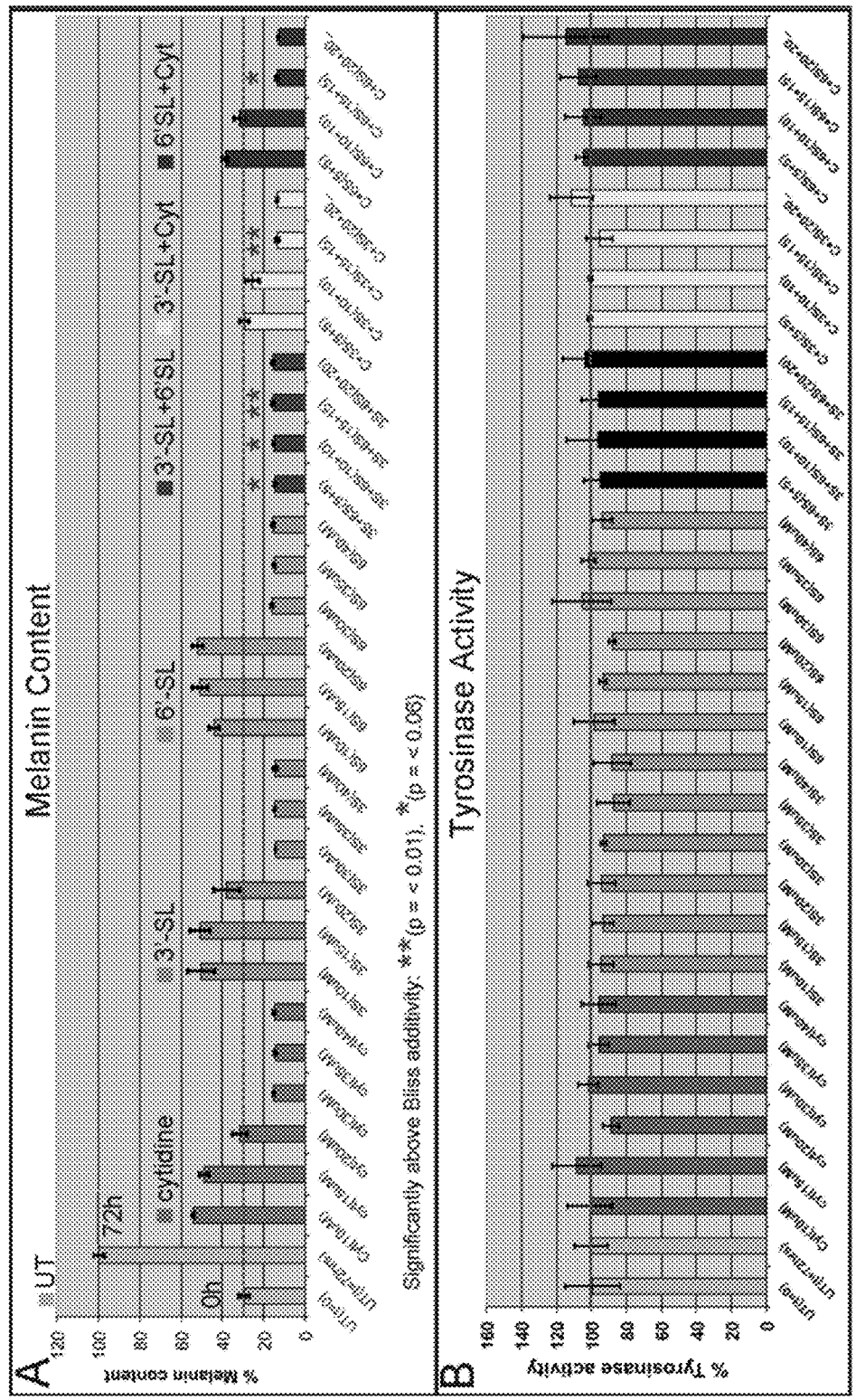
FIG. 8, comprising

Dose-response studies were carried out on melanocyte-keratinocyte co-cultures to compare the inhibitory activities of 6'-SL, 3'-SL, and cytidine on melanin content and tyrosinase activity, both as single agents and in combinations. All treatment categories caused highly significant reductions in melanin content at all concentrations tested (5-40 micromolar) (FIG. 8A; Table 3). At some concentrations treatments prevented new melanin synthesis during the 72 h experiment, i.e., melanin above the $t_0$ level at the beginning of the experiment (dashed line). In other cases, not only was new melanin content prevented but, unexpectedly, reduced below that seen at the $t_0$ level during the 72 h experiment (FIG. 8A, dashed line), implying that these treatments caused melanin degradation or release to the culture medium. The percent inhibition at each concentration was compared and analyzed for Bliss Additivity, i.e., significantly the same as the sum of the two agents alone (Fitzgerald et al., 2006, Nat Chem Biol 2:458-466; Ritz, C. & Streibig, J. C., 2005, Bioassay Analysis using R. J. Statist. Software, Vol 12, Issue 5.). While many of the treatment concentrations indeed showed Bliss Additivity, others showed synergism, i.e., inhibition significantly above that expected for Bliss Additivity. Synergism was seen in the combinations of 3'-SL+6'-SL (5+5 micromolar, 10+10 micromolar, 15+15 micromolar); 3'-SL+cytidine (15+15 micromolar); and 6'-SL+cytidine (15+15 micromolar), with P-values ranging from $p=\leq0.01$ to $p=\leq0.06$ (FIG. 8A, asterisks). In the same samples none of the agents significantly reduced tyrosinase activity (FIG. 8B). Together, the results indicate that the inhibitors reduced melanin content by targeting post-tyrosinase pathways, possibly through interference with glycosylation processes.

TABLE 3

P-Value Tests: treated vs untreated control*

| Treatment | Conc. (micromolar) | P-value vs. untreated control |
|---|---|---|
| cytidine | 15 | 0.0003 |
|  | 20 | 0.0001 |
|  | 30 | 0.0004 |
|  | 35 | 0.0005 |
|  | 40 | 0.0004 |
| 3'-SL | 10 | 0.0051 |
|  | 15 | 0.0077 |
|  | 20 | 0.0067 |
|  | 30 | 0.0004 |
|  | 35 | 0.0003 |
|  | 40 | 0.0006 |
| 6'-SL | 10 | 0.0002 |
|  | 15 | 0.0013 |
|  | 20 | 0.0027 |
|  | 30 | 0.0006 |
|  | 35 | 0.0003 |
|  | 40 | 0.0006 |
| Cyt + 3'-SL | 5 + 5 | 0.0002 |
|  | 10 + 10 | 0.0024 |
|  | 15 + 15 | 0.0002 |
|  | 20 + 20 | 0.0004 |
| Cyt + 6'-SL | 5 + 5 | 0.0007 |
|  | 10 + 10 | 0.0020 |
|  | 15 + 15 | 0.0005 |
|  | 20 + 20 | 0.0003 |
| 3'-SL + 6'-SL | 5 + 5 | 0.0003 |
|  | 10 + 10 | 0.0005 |
|  | 15 + 15 | 0.0002 |
|  | 20 + 20 | 0.0005 |

*P-values were determined by the Welch Two Sample t-test

The minimal doses for >80% inhibition of melanin content were determined for each treatment category. The combination of 6'-SL+3'-SL was the most effective, causing ~85% inhibition of melanin content at the combined concentration of 5 micromolar+5 micromolar, 3-fold more active than that in any other category (FIG. 8A, Table 4).

TABLE 4

Minimal treatment concentrations for >80% inhibition of melanin content*

| Treatment | Minimal concentration for >80% inhibition |
|---|---|
| Untreated Control | Not applicable |
| Single Agents |  |
| Cytidine | 30 micromolar |
| 6'-SL | 30 micromolar |
| 3'-SL | 30 micromolar |
| Combined Agents |  |
| Cytidine + 6'-SL | 15 micromolar + 15 micromolar |
| Cytidine + 3'-SL | 15 micromolar + 15 micromolar |
| 6'-SL + 3'-SL | 5 micromolar + 5 micromolar |

*Data are from FIG. 8A.

Effects of Cytidine, 6'-SL, 3'-SL on Melanin Transfer

Figure 9:
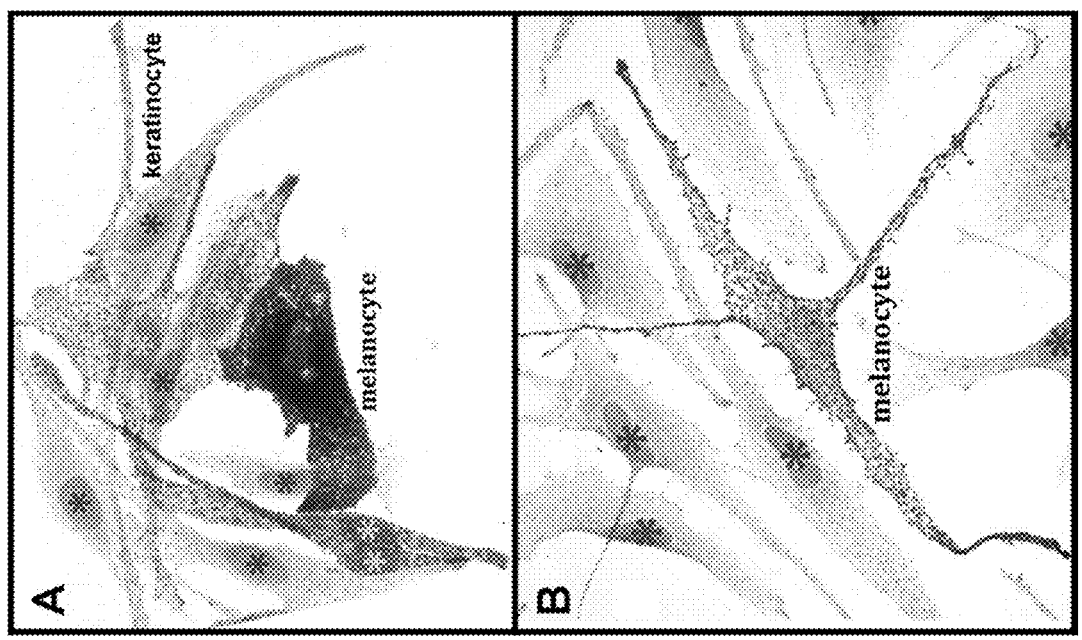
FIG. 9, comprising

The effects on melanocyte-keratinocyte melanosome transfer were assessed after treatment with cytidine, 3'-SL, and 6'-SL alone and in combination. FIG. 9A shows a representative field from untreated co-cultures with a highly melanized melanocyte surrounded by several keratinocytes. The melanocyte is packed with melanosomes and has close contacts with neighboring keratinocytes over large portions of the plasma membranes. The keratinocytes in direct contact with the melanocyte (nuclei with light asterisks) contain numerous cytoplasmic melanin granules transferred from the melanocyte. Keratinocytes not in contact with the melanocyte (nuclei with dark asterisks) contained notably fewer melanosomes. In contrast a representative field from a co-culture treated with the combination of 3'-SL+cytidine shows a marked reduction in melanocyte-keratinocyte contacts and a reduction of melanosomes in both cell types (FIG. 9B). All treatment categories showed these effects, but since transfer is a dynamic process, it could not be quantitated in the static fixed cultures studied herein. Together, the above results indicate that alone or in combination cytidine, 3'-SL, and 6'-SL (and/or botanical extracts containing these compounds) would be effective in reducing skin pigmentation.

Transfection of siRNAs for ST6 and ST3

Figure 10:
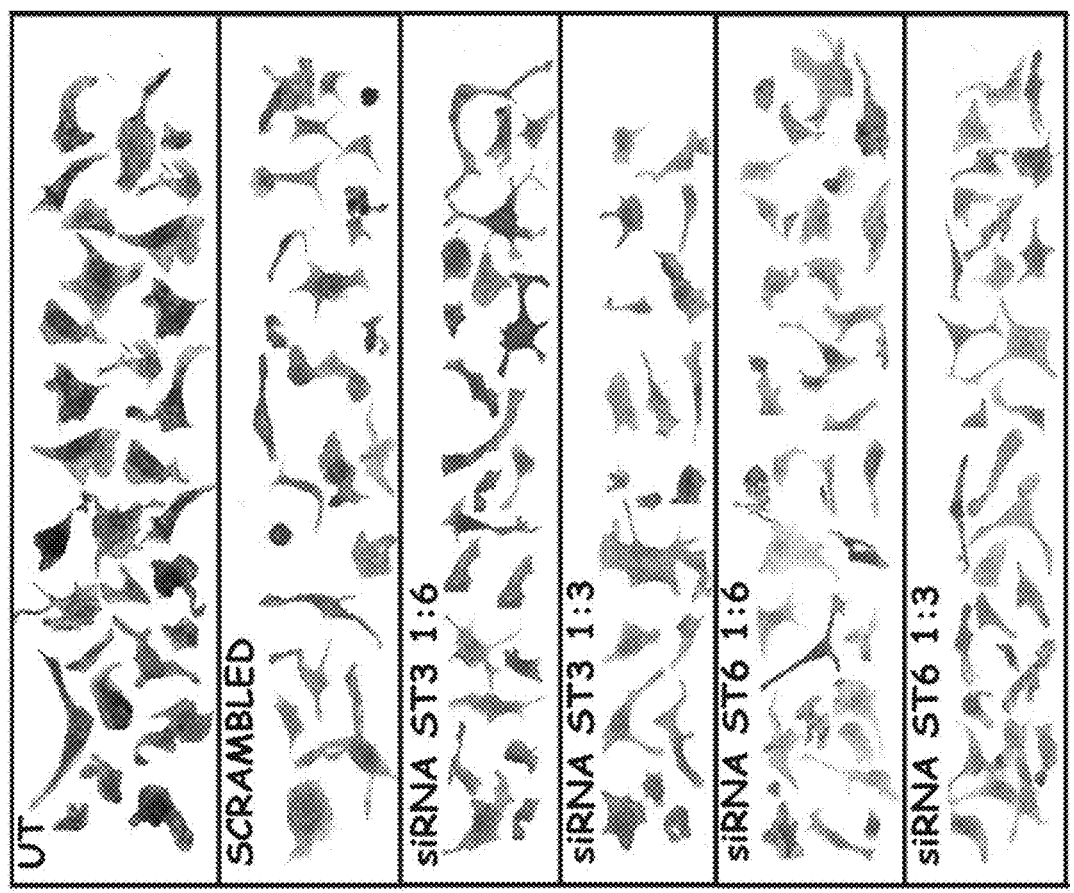
FIG. 10 is a set of images depicting the results of experiments demonstrating that ST6 siRNA and, to a lesser extent ST3 siRNA, reduced EBL binding in mouse melan-A cells (UT=untreated control).
Figure 11:
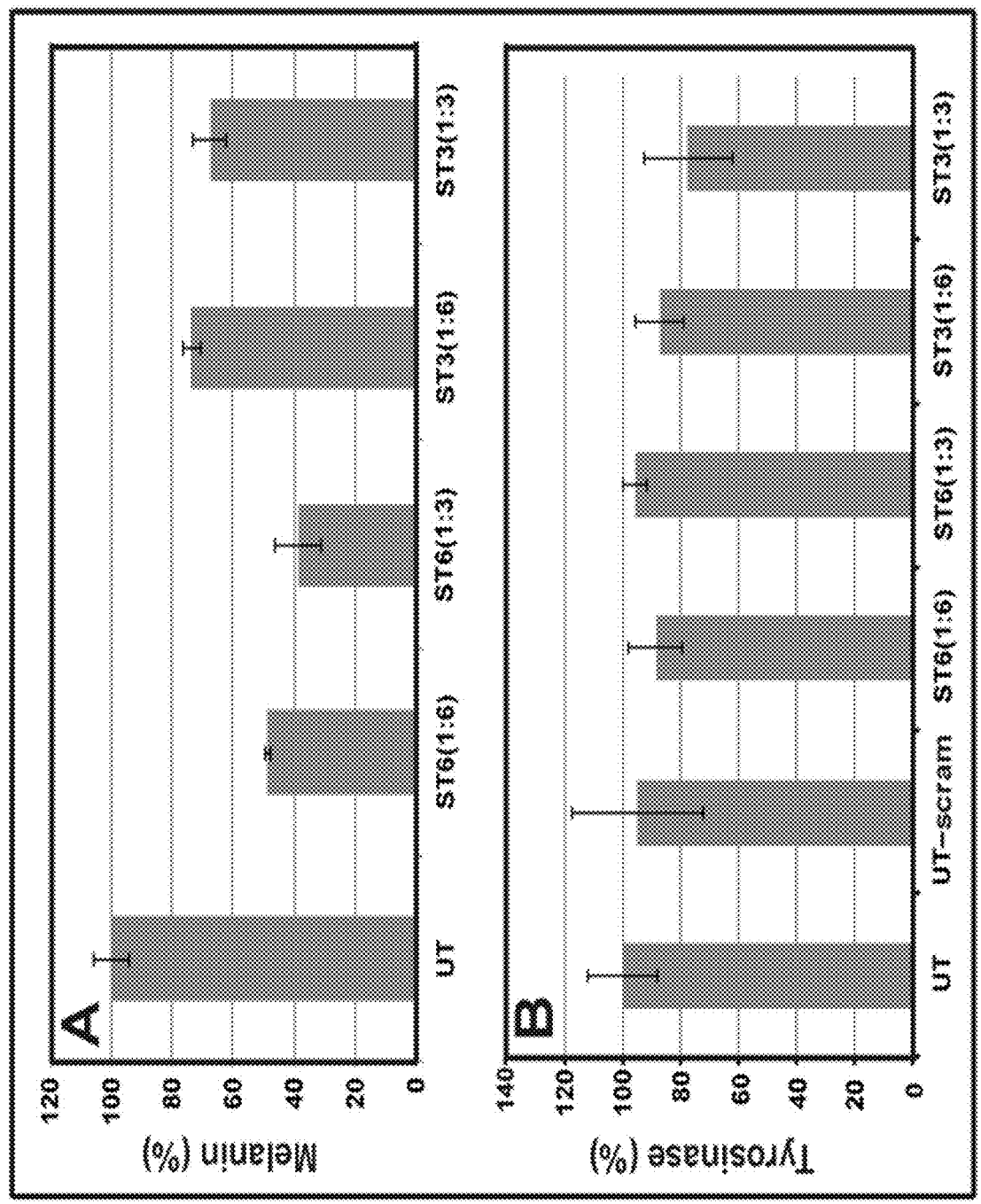
FIG. 11, comprising

When ST6 and ST3 siRNAs were transfected into mouse melan-A cells, both EBL binding (FIG. 10) and melanin production (FIG. 11) were strongly inhibited by ST6 siRNA and to some extent by ST3 siRNA. Together, these findings demonstrate that sialyl($\alpha$2,6)gal-terminated glycans play key roles in melanin synthesis and melanosome transfer to keratinocytes.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for reducing skin pigmentation consisting of administering to a subject in need of reduced skin pigmentation an effective amount of a composition consisting of an active ingredient having skin whitening activity and optionally one or more additional ingredients, wherein the active ingredient having skin whitening activity consists of 1% to 10% cytidine, and further wherein the one or more additional ingredients is selected from the group consisting of excipients; surface active agents; dispersing agents; inert diluents; granulating and disintegrating agents; lubricating agents; sweetening agents; flavoring agents; coloring agents; preservatives; gelatin; aqueous vehicles and solvents; oily vehicles and solvents; suspending agents; wetting agents; emulsifying agents, demulcents; thickening agents; antioxidants; antibiotics; antifungal agents; stabilizing agents; pharmaceutically acceptable polymeric materials and pharmaceutically acceptable hydrophobic materials.

2. The method of claim 1, wherein the active ingredient is 2% cytidine.

3. The method of claim 1, wherein the active ingredient is 3% cytidine.

4. The method of claim 1, wherein the active ingredient is 4% cytidine.

* * * * *